(12) United States Patent
Krouse et al.

(10) Patent No.: US 10,241,039 B2
(45) Date of Patent: *Mar. 26, 2019

(54) SPECTROSCOPIC ANALYSER

(71) Applicant: Klein Medical Limited, Auckland (NZ)

(72) Inventors: Donal Paul Krouse, Wellington (NZ); Raymond Andrew Simpkin, Auckland (NZ); Bryan James Smith, Auckland (NZ)

(73) Assignee: Klein Medical Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/377,914

(22) Filed: Dec. 13, 2016

(65) Prior Publication Data

US 2017/0184494 A1 Jun. 29, 2017

Related U.S. Application Data

(63) Continuation of application No. 14/110,134, filed as application No. PCT/NZ2012/000052 on Apr. 10, 2012, now Pat. No. 9,581,552.

(Continued)

(51) Int. Cl.
*G01N 21/35* (2014.01)
*G01J 3/10* (2006.01)
(Continued)

(52) U.S. Cl.
CPC ............ *G01N 21/3577* (2013.01); *G01J 3/10* (2013.01); *G01J 3/28* (2013.01); *G01J 3/42* (2013.01);
(Continued)

(58) Field of Classification Search
CPC ........ G01J 3/42; G01J 3/28; G01J 2003/1286; G01N 21/3577; G01N 21/84; G01N 2021/3595; G01N 2201/0691
(Continued)

(56) References Cited

U.S. PATENT DOCUMENTS

| 249,881 A | 11/1881 | Bourgmeyer |
| 1,426,551 A | 8/1922 | Cress |

(Continued)

FOREIGN PATENT DOCUMENTS

| EP | 0025491 B1 | 1/1986 |
| EP | 0509955 A2 | 10/1992 |

(Continued)

OTHER PUBLICATIONS

Int'l Search Report and Written Opinion for related Int'l App No. PCT/NZ2012/000052, filed Apr. 10, 2012, published Aug. 2, 2012.

(Continued)

*Primary Examiner* — David Porta
*Assistant Examiner* — Blake Riddick
(74) *Attorney, Agent, or Firm* — Knobbe, Martens, Olson & Bear, LLP

(57) ABSTRACT

An analyser 10 for identifying or verifying or otherwise characterising a liquid based drug sample 16 comprising: an electromagnetic radiation source 11 for emitting electromagnetic radiation 14a in at least one beam at a sample 16, the electromagnetic radiation comprising at least two different wavelengths, a sample detector 17 that detects affected electromagnetic radiation resulting from the emitted electromagnetic radiation affected by the sample, and a processor 18 for identifying or verifying the sample from the detected affected electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

18 Claims, 17 Drawing Sheets

Related U.S. Application Data

(60) Provisional application No. 61/472,290, filed on Apr. 6, 2011.

(51) Int. Cl.
  *G01J 3/28* (2006.01)
  *G01J 3/42* (2006.01)
  *G01N 21/84* (2006.01)
  *G01N 21/3577* (2014.01)
  *G01N 21/359* (2014.01)
  *G01J 3/12* (2006.01)

(52) U.S. Cl.
  CPC ............ *G01N 21/359* (2013.01); *G01N 21/84* (2013.01); *G01J 2003/1286* (2013.01); *G01N 2021/3595* (2013.01); *G01N 2201/0612* (2013.01); *G01N 2201/0691* (2013.01)

(58) Field of Classification Search
  USPC ............ 250/339.07, 339.12, 339.08, 339.09; 356/301
  See application file for complete search history.

(56) References Cited

U.S. PATENT DOCUMENTS

| | | |
|---|---|---|
| 1,776,739 A | 9/1930 | O'Brien |
| 1,881,354 A | 10/1932 | Everett |
| 2,168,579 A | 8/1939 | Perreton |
| 2,448,986 A | 9/1948 | Ladwig |
| 2,807,034 A | 9/1957 | Lloyd |
| 3,068,496 A | 12/1962 | Owens |
| 3,091,780 A | 6/1963 | Smithson |
| 3,204,500 A | 9/1965 | Lincoln |
| 3,293,672 A | 12/1966 | Gregersen |
| 3,394,426 A | 7/1968 | Knox |
| 3,735,433 A | 5/1973 | Smith |
| 3,737,931 A | 6/1973 | Hodgson |
| 3,950,100 A | 4/1976 | Keene et al. |
| 4,012,145 A | 3/1977 | Chabannes |
| 4,158,505 A | 6/1979 | Mathisen et al. |
| 4,195,379 A | 4/1980 | Krasnik |
| 4,328,743 A | 5/1982 | Fager |
| 4,359,622 A * | 11/1982 | Dostoomian ........ B23K 11/252 219/109 |
| 4,520,519 A | 6/1985 | Kuehl |
| 4,564,761 A | 1/1986 | Buckwald |
| 4,678,569 A | 7/1987 | Cunningham |
| 4,832,491 A | 5/1989 | Sharpe et al. |
| 5,060,248 A | 10/1991 | Dumoulin |
| 5,099,123 A | 3/1992 | Harjunmaa |
| 5,178,142 A | 1/1993 | Harjunmaa |
| 5,187,368 A | 2/1993 | Galante et al. |
| 5,285,260 A | 2/1994 | Dumoulin |
| 5,285,261 A | 2/1994 | Dumoulin |
| 5,345,395 A | 9/1994 | Griner |
| 5,348,002 A | 9/1994 | Caro |
| 5,348,003 A | 9/1994 | Caro |
| 5,355,880 A | 10/1994 | Thomas et al. |
| 5,357,343 A | 10/1994 | Lowne et al. |
| 5,406,377 A | 4/1995 | Dumoulin |
| 5,446,534 A | 8/1995 | Goldman |
| 5,602,647 A | 2/1997 | Xu et al. |
| 5,614,719 A | 3/1997 | Hayes |
| 5,647,359 A | 7/1997 | Kohno et al. |
| 5,682,027 A * | 10/1997 | Bertina ................. G06K 7/0008 235/380 |
| 5,712,165 A | 1/1998 | Alvarez et al. |
| 5,818,048 A * | 10/1998 | Sodickson ............ A61B 5/0059 250/343 |
| 5,920,393 A | 7/1999 | Kaplan |
| 6,157,455 A | 12/2000 | Pinvidic et al. |
| 6,319,668 B1 | 11/2001 | Nova |
| 6,483,589 B1 | 11/2002 | Suzuki et al. |
| 6,643,016 B2 | 11/2003 | Garver et al. |
| 6,771,369 B2 | 8/2004 | Rzasa et al. |
| 6,847,899 B2 | 1/2005 | Allgeyer |
| 7,006,214 B2 | 2/2006 | Rzasa et al. |
| 7,063,592 B2 | 6/2006 | Pointer |
| 7,154,599 B2 | 12/2006 | Adams et al. |
| 7,218,395 B2 | 5/2007 | Kaye et al. |
| 7,417,729 B2 | 8/2008 | Greenwald |
| 7,460,226 B2 | 12/2008 | Klein |
| 7,651,851 B2 | 1/2010 | Clarke |
| 7,764,372 B2 | 7/2010 | Moran, Jr. et al. |
| 7,840,360 B1 | 11/2010 | Micheels et al. |
| 7,985,118 B2 | 7/2011 | Bermel |
| 8,164,050 B2 | 4/2012 | Ford et al. |
| 8,512,279 B2 | 8/2013 | Klein |
| 9,354,165 B2 | 5/2016 | Simpkin et al. |
| 9,581,552 B2 | 2/2017 | Krouse et al. |
| 2002/0059159 A1 | 5/2002 | Cook |
| 2002/0179929 A1 | 12/2002 | Takahashi et al. |
| 2003/0095736 A1 | 5/2003 | Kish et al. |
| 2003/0227628 A1 | 12/2003 | Kreimer et al. |
| 2005/0099624 A1 | 5/2005 | Staehr et al. |
| 2005/0099632 A1 | 5/2005 | Harper |
| 2005/0124863 A1 | 6/2005 | Cook |
| 2005/0162653 A1 | 7/2005 | Carver et al. |
| 2006/0077860 A1* | 4/2006 | Nagatomi ............ G11B 7/1275 369/112.03 |
| 2006/0240401 A1 | 10/2006 | Clarke |
| 2006/0270919 A1 | 11/2006 | Brenner |
| 2007/0086625 A1 | 4/2007 | Polli |
| 2007/0103678 A1 | 5/2007 | Sterling et al. |
| 2007/0142777 A1 | 6/2007 | Klein |
| 2007/0159636 A1 | 7/2007 | Jayaraman |
| 2007/0178596 A1 | 8/2007 | Babichenko |
| 2007/0182960 A1 | 8/2007 | Jayaraman |
| 2007/0201025 A1 | 8/2007 | Greenwald |
| 2007/0232189 A1 | 10/2007 | Hamby |
| 2008/0055587 A1* | 3/2008 | Scherer ................. G01T 1/40 356/73 |
| 2008/0165357 A1* | 7/2008 | Stern ................. G01B 11/0608 356/364 |
| 2008/0218733 A1* | 9/2008 | Benes ..................... G01J 3/02 356/51 |
| 2009/0097025 A1 | 4/2009 | Iddan |
| 2009/0177407 A1 | 7/2009 | Lennernas |
| 2009/0216462 A1* | 8/2009 | Tate .................. G01N 21/3504 702/24 |
| 2009/0303475 A1 | 12/2009 | Jayaraman et al. |
| 2010/0208261 A1 | 8/2010 | Sens et al. |
| 2010/0261409 A1 | 10/2010 | Bermel |
| 2011/0019183 A1 | 1/2011 | Ukon et al. |
| 2011/0181867 A1 | 7/2011 | Tracton et al. |
| 2012/0095711 A1 | 4/2012 | Foster et al. |
| 2012/0143142 A1 | 6/2012 | Klein |
| 2013/0265566 A1 | 10/2013 | Smith et al. |
| 2013/0345640 A1 | 12/2013 | Klein |
| 2016/0131572 A1 | 5/2016 | Klein |
| 2016/0265972 A1 | 9/2016 | Simpkin et al. |
| 2016/0320295 A1 | 11/2016 | Smith et al. |

FOREIGN PATENT DOCUMENTS

| | | |
|---|---|---|
| EP | 1545659 B1 | 7/2008 |
| EP | 2314156 A1 | 4/2011 |
| ES | 2338745 | 5/2010 |
| GB | 482237 A | 3/1938 |
| JP | 2004-535297 A | 11/2004 |
| JP | 4566743 B2 | 10/2010 |
| WO | WO 01/16578 | 3/2001 |
| WO | WO 02/074162 | 9/2002 |
| WO | WO 03/079267 | 9/2003 |
| WO | WO 03/106981 | 12/2003 |
| WO | WO 2004/033003 | 4/2004 |
| WO | WO 2004/054353 | 7/2004 |
| WO | WO 2005/046766 | 5/2005 |
| WO | WO 2005/067110 | 7/2005 |
| WO | WO 2012/114136 | 8/2012 |
| WO | WO 2012/138236 | 10/2012 |

(56) References Cited

FOREIGN PATENT DOCUMENTS

OTHER PUBLICATIONS

Specification (excluding drawings) of U.S. Appl. No. 61/061,803, Titled "Broadband Spectrophotometer" in 50 pages, filed Jun. 16, 2008.
Specification (excluding drawings) of U.S. Appl. No. 61/233,291, Titled "Broadband Spectrophotometer" in 49 pages, filed Aug. 12, 2009.
Specification (excluding drawings) of U.S. Appl. No. 61/251,963, Titled "Improvements in Sample Analysis" in 58 pages, filed Oct. 15, 2009.
Specification (excluding drawings) of U.S. Appl. No. 61/393,991, Titled "Broadband Spectrophotometer" in 40 pages, filed Oct. 18, 2010.
U.S. Appl. No. 61/472,290, filed Apr. 6, 2011.
U.S. Appl. No. 61/661,573, filed Jun. 19, 2012.
U.S. Appl. No. 61/710,585, filed Oct. 5, 2012.

* cited by examiner

Test Results for 30 Drugs

| | Me | He | Ma | Ma | Do | Co | No | In | Po | Vo | Pl | Os | Zo | Gl | Ge | Be | At | De | Ci | Xy | Na | Ad | Ne | Va | Tr | Es | Pr | Mi | Mi | Te | Error |
|---|---|---|---|---|---|---|---|---|---|---|---|---|---|---|---|---|---|---|---|---|---|---|---|---|---|---|---|---|---|---|---|
| Metar | 0 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0.000 |
| Hepar | 15 | 0 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0.000 |
| Marca | 15 | 15 | 0 | 15 | 15 | 15 | 15 | 15 | 15 | 15 | 15 | 15 | 15 | 15 | 15 | 14 | 14 | 15 | 15 | 15 | 15 | 13 | 14 | 15 | 14 | 15 | 15 | 13 | 14 | 15 | 0.028 |
| Magne | 15 | 15 | 15 | 0 | 15 | 15 | 15 | 15 | 15 | 15 | 15 | 15 | 12 | 15 | 15 | 15 | 15 | 15 | 15 | 15 | 15 | 15 | 15 | 15 | 15 | 15 | 15 | 15 | 15 | 15 | 0.002 |
| Dopam | 15 | 15 | 15 | 15 | 0 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0.000 |
| Corda | 15 | 15 | 15 | 0 | 0 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0.000 |
| Norad | 15 | 15 | 15 | 15 | 15 | 15 | 0 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0.000 |
| Insul | 15 | 15 | 15 | 15 | 15 | 15 | 15 | 3 | 15 | 15 | 15 | 15 | 15 | 15 | 15 | 15 | 15 | 5 | 15 | 15 | 15 | 15 | 15 | 15 | 15 | 15 | 15 | 15 | 15 | 15 | 0.023 |
| Potas | 15 | 15 | 15 | 6 | 15 | 15 | 15 | 15 | 0 | 15 | 0 | 15 | 14 | 15 | 15 | 15 | 15 | 15 | 15 | 15 | 15 | 15 | 15 | 15 | 15 | 15 | 15 | 15 | 15 | 15 | 0.002 |
| Voluv | 15 | 15 | 15 | 6 | 15 | 15 | 15 | 15 | 15 | 0 | 15 | 15 | 15 | 15 | 15 | 15 | 15 | 15 | 15 | 15 | 15 | 15 | 15 | 15 | 15 | 0 | 15 | 15 | 15 | 15 | 0.021 |
| Plasm | 15 | 15 | 15 | 15 | 15 | 15 | 15 | 15 | 15 | 15 | 0 | 15 | 15 | 15 | 15 | 15 | 15 | 15 | 15 | 15 | 15 | 15 | 15 | 15 | 15 | 15 | 15 | 15 | 12 | 15 | 0.007 |
| Osmit | 15 | 15 | 15 | 15 | 15 | 15 | 15 | 15 | 15 | 15 | 15 | 0 | 15 | 15 | 15 | 15 | 15 | 15 | 15 | 15 | 15 | 15 | 15 | 15 | 15 | 15 | 15 | 15 | 15 | 15 | 0.000 |
| Zofra | 15 | 2 | 15 | 15 | 15 | 15 | 15 | 15 | 14 | 15 | 15 | 15 | 1 | 15 | 15 | 9 | 8 | 15 | 15 | 0 | 11 | 7 | 15 | 14 | 15 | 15 | 15 | 6 | 15 | 15 | 0.113 |
| Gluco | 15 | 15 | 15 | 15 | 15 | 15 | 15 | 15 | 15 | 15 | 15 | 15 | 15 | 0 | 15 | 15 | 15 | 15 | 15 | 15 | 15 | 15 | 15 | 15 | 15 | 15 | 15 | 15 | 15 | 15 | 0.000 |
| Gelof | 15 | 15 | 15 | 15 | 15 | 15 | 15 | 15 | 15 | 15 | 15 | 15 | 15 | 15 | 0 | 15 | 0 | 15 | 15 | 15 | 15 | 2 | 15 | 15 | 15 | 15 | 15 | 4 | 15 | 15 | 0.168 |
| Betal | 15 | 14 | 3 | 15 | 15 | 15 | 15 | 15 | 15 | 15 | 15 | 15 | 6 | 15 | 15 | 0 | 12 | 15 | 14 | 10 | 11 | 2 | 15 | 15 | 14 | 15 | 15 | 15 | 14 | 15 | 0.030 |
| Atrop | 15 | 15 | 10 | 15 | 15 | 15 | 15 | 15 | 15 | 15 | 12 | 15 | 12 | 15 | 15 | 12 | 0 | 15 | 15 | 15 | 15 | 15 | 15 | 15 | 14 | 15 | 15 | 15 | 14 | 15 | 0.018 |
| Dexam | 15 | 15 | 15 | 15 | 15 | 15 | 15 | 7 | 15 | 15 | 15 | 15 | 15 | 15 | 15 | 15 | 15 | 0 | 15 | 15 | 15 | 15 | 15 | 0 | 15 | 15 | 15 | 15 | 15 | 15 | 0.009 |
| Citan | 15 | 15 | 15 | 15 | 15 | 15 | 15 | 15 | 15 | 14 | 15 | 15 | 15 | 15 | 13 | 15 | 15 | 15 | 0 | 15 | 15 | 15 | 14 | 15 | 15 | 15 | 0 | 15 | 15 | 15 | 0.005 |
| Xyloc | 15 | 15 | 15 | 15 | 15 | 15 | 15 | 15 | 15 | 15 | 15 | 15 | 5 | 15 | 15 | 15 | 15 | 15 | 15 | 0 | 0 | 15 | 15 | 15 | 15 | 10 | 15 | 0 | 15 | 15 | 0.002 |
| Narop | 15 | 15 | 15 | 15 | 15 | 15 | 15 | 15 | 15 | 13 | 15 | 15 | 15 | 14 | 15 | 8 | 10 | 15 | 15 | 14 | 0 | 0 | 12 | 15 | 15 | 15 | 15 | 13 | 15 | 15 | 0.018 |
| Adren | 15 | 13 | 15 | 15 | 15 | 15 | 15 | 15 | 15 | 15 | 2 | 15 | 9 | 15 | 15 | 15 | 14 | 15 | 13 | 15 | 15 | 0 | 6 | 15 | 15 | 14 | 0 | 9 | 15 | 15 | 0.060 |
| Neost | 15 | 14 | 15 | 15 | 15 | 15 | 15 | 15 | 15 | 15 | 15 | 15 | 15 | 15 | 15 | 15 | 15 | 15 | 15 | 15 | 15 | 15 | 0 | 15 | 15 | 15 | 15 | 15 | 15 | 15 | 0.000 |
| Valoi | 15 | 15 | 15 | 15 | 15 | 15 | 15 | 15 | 15 | 15 | 12 | 15 | 12 | 15 | 15 | 15 | 12 | 15 | 15 | 15 | 15 | 15 | 15 | 0 | 14 | 15 | 15 | 13 | 14 | 15 | 0.041 |
| Trand | 15 | 11 | 14 | 15 | 15 | 15 | 15 | 15 | 15 | 15 | 15 | 15 | 15 | 15 | 15 | 15 | 15 | 15 | 15 | 15 | 15 | 15 | 15 | 15 | 0 | 0 | 15 | 15 | 15 | 15 | 0.000 |
| Esmol | 15 | 15 | 15 | 15 | 15 | 15 | 15 | 15 | 15 | 15 | 15 | 15 | 5 | 15 | 15 | 5 | 13 | 15 | 8 | 10 | 14 | 6 | 1 | 15 | 10 | 0 | 15 | 0 | 15 | 15 | 0.000 |
| Propo | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0 | 15 | 15 | 15 | 0.000 |
| Midaz | 15 | 8 | 4 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0 | 15 | 15 | 0.221 |
| Mivac | 15 | 12 | 15 | 15 | 15 | 15 | 15 | 15 | 15 | 15 | 2 | 15 | 15 | 15 | 15 | 14 | 14 | 15 | 15 | 15 | 13 | 15 | 15 | 14 | 15 | 15 | 15 | 15 | 1 | 15 | 0.046 |
| Tenox | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 15 | 0 | 0.000 |

FIGURE 15

SPECTROSCOPIC ANALYSER

CROSS-REFERENCE TO RELATED APPLICATIONS

This application is a continuation of U.S. patent application Ser. No. 14/110,134, filed May 19, 2014, which is a U.S. National Phase under 35 U.S.C. § 371 of Intl Appl. No. PCT/NZ2012/000052, filed Apr. 10, 2012, designating the United States and published in English on Oct. 11, 2012 as WO 2012/138236, which claims the benefit of priority to U.S. Provisional Appl. No. 61/472,290 filed Apr. 6, 2011. Any and all applications for which a foreign or domestic priority claim is identified in the Application Data Sheet as filed with the present application are hereby incorporated by reference under 37 C.F.R. § 1.57.

BACKGROUND

Field

The present invention relates to a spectroscopic analyser, such as a spectrophotometer, for verifying and/or identifying or otherwise analysing drugs, blood or other substances.

Description of the Related Art

Spectroscopy, for example through the use of a spectroscopic analyser such as a spectrophotometer, can be used to analyse substances. For example, by directing incident radiation towards a sample, and analysing the spectral nature of the affected radiation, it can be possible to gain an indication of the nature of the sample.

However, such analysers often provide inaccurate analysis. Accurately discriminating between different substances can be difficult.

SUMMARY

It is an object of the present invention to provide an analyser and/or method for verifying or identifying or otherwise characterising a drug or other substances using spectroscopy.

In one aspect the present invention may be said to consist in an analyser for identifying or verifying a liquid based drug sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample and provides output representing the detected affected radiation, and a processor for identifying or verifying the sample from the detector output representing the detected affected electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Described herein is verifying or identifying the drug sample is against comparison data for one of a set of n drugs, and wherein the electromagnetic radiation comprises at least $\log_2 n$ different wavelengths in one or more beams.

Preferably the different wavelengths span or capture a plurality of at least some of the spectral characteristics in the liquid spectrum between 1300 nm and 2000 nm.

Preferably the liquid spectrum comprises two or more spectral characteristics, and wherein: each spectral characteristic falls in or spans a region of the liquid spectrum, each wavelength falls within one of the regions.

Described herein is each region is defined by a wavelength range.

Preferably the spectral characteristics comprise peaks, troughs, inflections, stable points or regions plateaus, knees and/or slopes of the liquid spectrum.

Preferably the liquid is water and comprises spectral characteristics falling in the following regions of the water spectrum: a first region between 1300 nm and 1400 nm, a second region between 1400 nm and 1500 nm, a third region between 1500 nm and 1600 nm, a fourth region between 1600 nm and 1700 nm, a fifth region between 1700 nm and 1800 nm, and a sixth region between 1800 nm and 200 nm.

Described herein is the electromagnetic radiation has an anchor wavelength in the vicinity of the wavelength(s) of (or within a region spanning) a stable region in the liquid spectrum.

Described herein is each wavelength further corresponds to a wavelength produced by a source that is readily/cheaply obtainable.

Described herein is the source is a plurality of lasers, each laser configured to emit an electromagnetic radiation beam at a fixed or tuneable wavelength.

Preferably comprises a modulator for modulating the electromagnetic radiation beam(s) emitted at the sample resulting in detected affected radiation detected by the sample detector that is modulated wherein the processor as part of identifying or verifying the sample from the output from the detector removes the dark current component from the output representing the detected affected modulated electromagnetic radiation Optionally the processor removes the dark current component by multiplying the output representing the detected affected modulated electromagnetic radiation by sine and cosine functions and integrating over the period of modulation oscillation to remove the dark current component.

Optionally the processor removes the dark current component by conducting a Fourier Transform on the output representing the modulated detected affected radiation and removing the dark current component from the transformed.

Described herein is the processor identifies or verifies the drug sample using reference information.

Described herein is the affected electromagnetic radiation at or the electromagnetic radiation beam comprising the anchor wavelength provides the reference information.

Described herein is the analyser further comprises: an optical device for directing the plurality of electromagnetic radiation beams to a reference sample, a reference detector that detects affected electromagnetic radiation beams affected by the reference sample to obtain the reference information and that passes the reference information to the processor.

Described herein is the detector and/or source are temperature compensated to provide temperature stability, preferably using thermistors and peltier devices in a closed loop system.

Described herein is each electromagnetic radiation beam is a high intensity narrowband light beam.

Described herein is the detector is a broadband photodiode that is biased to have a response corresponding to the wavelengths of the affected radiation.

Described herein is the emitted electromagnetic radiation beams from the plurality of lasers are directed to a sample path by one or more of: a carousel or carriage device to position the laser beams in the sample path, or a prism, diffraction grating, beam splitter or other optical device to redirect a radiation beam along the sample path.

Described herein is the processor receives: output representing the affected electromagnetic radiation from the drug sample which provides drug sample information, and optionally reference information for each wavelength, and the processor: determines a representative value of the drug sample information using that information and optionally reference information for each wavelength.

Described herein is the sample information and reference information correlate intensity and wavelength for each electromagnetic radiation beam.

Described herein is the representative value corresponds to a best fit between the sample information and optionally the reference information.

Described herein is the representative value for the electromagnetic radiation beam for each wavelength is compared to stored values to verify or identify the drug sample.

Described herein is the liquid is water, there are six electromagnetic radiation beams and the wavelengths are substantially 1350 nm, 1450 nm, 1550, nm, 1650, nm, 1750 nm and 1850 nm, and optionally wherein 1450 nm is the anchor wavelength.

Described herein is the sample is in an intravenous delivery device such as an IV infusions set or syringe, or other receptacle such as a test-cell, test-tube, flow cell or the like.

Preferably the source is a laser comprising a photodetector, wherein the photodetector detects electromagnetic radiation from the laser and outputs the reference information.

In another aspect the present invention may be said to consist in a method for identifying or verifying or otherwise characterising a liquid based drug sample comprising: emitting electromagnetic radiation in at least one beam at a sample, the electromagnetic radiation comprising at least two different wavelengths, detecting affected electromagnetic radiation resulting from the emitted electromagnetic radiation affected by the sample and providing output representing the detected affected radiation, and identifying or verifying the sample from the output representing detected affected electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Described herein is verifying or identifying the drug sample is against comparison data for one of a set of n drugs, and wherein the electromagnetic radiation comprises at least $\log_2 n$ different wavelengths in one or more beams.

Preferably the different wavelengths span or capture a plurality of at least some of the spectral characteristics in the liquid spectrum between 1300 nm and 2000 nm.

Preferably the liquid spectrum comprises two or more spectral characteristics, and wherein: each spectral characteristic falls in or spans a region of the liquid spectrum, each wavelength falls within one of the regions.

Described herein is each region is defined by a wavelength range.

Preferably the spectral characteristics comprise peaks, troughs, inflections, stable points or regions, plateaus, knees and/or slopes of the liquid spectrum.

Preferably the liquid is water and comprises spectral characteristics falling in the following regions of the water spectrum: a first region between 1300 nm and 1400 nm, a second region between 1400 nm and 1500 nm, a third region between 1500 nm and 1600 nm, a fourth region between 1600 nm and 1700 nm, a fifth region between 1700 nm and 1800 nm, and a sixth region between 1800 nm and 200 nm.

Described herein is the electromagnetic radiation has an anchor wavelength in the vicinity of the wavelength(s) of (or within a region spanning) a stable region in the liquid spectrum.

Described herein is each wavelength further corresponds to a wavelength produced by a source that is readily/cheaply obtainable.

Described herein is the electromagnetic radiation is generated using a source comprising a plurality of lasers, each laser configured to emit an electromagnetic radiation beam at a fixed or tuneable wavelength.

Described herein is wherein a modulator is used for modulating the electromagnetic radiation beams emitted at the sample resulting in detected affected radiation that is modulated, and wherein identifying or verifying the sample from the output from the output comprises removing the dark current component from the output representing the detected affected modulated electromagnetic radiation.

Described herein is removing the dark current component comprises multiplying the output representing the detected affected modulated electromagnetic radiation by sine and cosine functions and integrating over the period of modulation oscillation to remove the dark current component.

Described herein is removing the dark current component comprises conducting a Fourier Transform on the output representing the modulated detected affected radiation and removing the dark current component from the transformed.

Described herein is the identifying or verifying is carried out by a processor that identifies or verifies the drug sample using reference information.

Described herein is the affected electromagnetic radiation at or the electromagnetic radiation beam comprising the anchor wavelength provides the reference information.

Described herein is the method further comprises: directing the plurality of electromagnetic radiation beams to a reference sample using an optical device, detecting using a reference detector affected electromagnetic radiation beams affected by the reference sample to obtain the reference information and that passes the reference information to the processor.

Described herein is the method further comprises temperature compensating the detector and/or source provide temperature stability, preferably using thermistors and peltier devices in a closed loop system.

Described herein is each electromagnetic radiation beam is a high intensity narrowband light beam.

Described herein is the detector is a broadband photodiode that is biased to have a response corresponding to the wavelength/s of the affected radiation.

Described herein is the emitted electromagnetic radiation beams from the plurality of lasers are directed to a sample path by one or more of: a carousel or carriage device to position the laser beams in the sample path, or a prism, diffraction grating, beam splitter or other optical device to redirect a radiation beam along the sample path.

Described herein is the processor receives: affected electromagnetic radiation from the drug sample which provides drug sample information, and optionally reference information for each wavelength, and the processor: determines a representative value of the drug sample information and optionally reference information for each wavelength.

Described herein is the sample information and reference information correlate intensity and wavelength for each electromagnetic radiation beam.

Described herein is the representative value corresponds to a best fit between the sample information and optionally the reference information.

Described herein is the representative value for the electromagnetic radiation beam for each wavelength is compared to stored values to verify or identify the drug sample.

Described herein is the liquid is water, there are six electromagnetic radiation beams and the wavelengths are substantially 1350 nm, 1450 nm, 1550, nm, 1650, nm, 1750 nm and 1850 nm, wherein 1450 nm is the anchor wavelength.

Described herein is the sample is in an intravenous delivery device such as an IV infusions set or syringe, or other receptacle such as a test-cell, test-tube, flow cell or the like.

Preferably each laser comprises a photodetector, wherein the photodetector detects electromagnetic radiation from the laser and outputs the reference information.

In another aspect the present invention may be said to consist in an analyser for identifying or verifying or otherwise characterising a drug sample (or other substance) in a liquid carrier comprising: an electromagnetic radiation source for emitting electromagnetic radiation in at least one beam at a sample, the electromagnetic radiation comprising at least two different selected wavelengths, a sample detector that detects affected electromagnetic radiation resulting from the emitted electromagnetic radiation affected by the sample, and a processor for identifying or verifying the sample from the detected affected electromagnetic radiation, wherein each wavelength is selected to be in the vicinity of the wavelength(s) of (or within a region spanning) a spectral characteristic in the spectrum of the liquid carrier, each wavelength falling within an analysis range suitable for the liquid carrier.

In another aspect the present invention may be said to consist in a method for identifying or verifying or otherwise characterising a drug sample (or other substance) in a liquid carrier comprising: emitting electromagnetic radiation in at least one beam at a sample, the electromagnetic radiation comprising at least two different selected wavelengths, detecting affected electromagnetic radiation resulting from the emitted electromagnetic radiation affected by the sample, and identifying or verifying the sample from the detected affected electromagnetic radiation, wherein each wavelength is selected to be in the vicinity of the wavelength(s) of (or within a region spanning) a spectral characteristic in the spectrum of the liquid carrier, each wavelength falling within an analysis range suitable for the liquid carrier.

Described herein is an analyser, for identifying or verifying or otherwise characterising a liquid based drug sample (or other substance) comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample, and a processor for identifying or verifying the sample from the detected affected electromagnetic radiation, wherein each wavelength is falls in an analysis range that provides improved identification/verification for drugs in the liquid carrier, and each wavelength is in the vicinity of the wavelength(s) of (or within a region spanning) a spectral characteristic in the liquid spectrum in the analysis range.

Described herein is a method for identifying or verifying or otherwise characterising a liquid based drug sample (or other substance) comprising: emitting electromagnetic radiation in at least one beam at a sample, the electromagnetic radiation comprising at least two different wavelengths, detecting affected electromagnetic radiation resulting from the emitted electromagnetic radiation affected by the sample, and identifying or verifying the sample from the detected affected electromagnetic radiation, wherein each wavelength is falls in an analysis range that provides improved identification/verification for drugs in the liquid carrier, and each wavelength is in the vicinity of the wavelength(s) of (or within a region spanning) a spectral characteristic in the liquid spectrum in the analysis range.

In another aspect the present invention an analyser for identifying or verifying or otherwise characterising a liquid based drug sample comprising: an electromagnetic radiation source for emitting modulated electromagnetic radiation in at least one beam at a sample, the electromagnetic radiation comprising at least two different wavelengths, a sample detector that detects affected modulated electromagnetic radiation resulting from the emitted electromagnetic radiation affected by the sample and provides output representing the detected affected modulated radiation, and a processor for identifying or verifying the sample from the output representing detected affected modulated electromagnetic radiation including removing dark current from the output, wherein each wavelength or at least two of the wavelengths is between substantially 1300 nm and 2000 nm.

In another aspect the present invention a method for identifying or verifying or otherwise characterising a liquid based drug sample comprising: emitting modulated electromagnetic radiation in at least one beam at a sample, the electromagnetic radiation comprising at least two different wavelengths, detecting affected modulated electromagnetic radiation resulting from the emitted electromagnetic radiation affected by the sample and providing output representing the detected affected radiation, and identifying or verifying the sample from the output representing detected affected modulated electromagnetic radiation including removing dart current from the output, wherein each wavelength or at least two of the wavelengths is between substantially 1300 nm and 2000 nm.

Described herein is an analyser for identifying or verifying or otherwise characterising a liquid based drug sample comprising: an electromagnetic radiation source for emitting electromagnetic radiation in at least one beam at a sample, the electromagnetic radiation comprising at least two different wavelengths and for measuring the power of the emitted electromagnetic radiation, a sample detector that detects affected electromagnetic radiation resulting from the emitted electromagnetic radiation affected by the sample and provides output representing the detected affected radiation, and a processor for identifying or verifying the sample from the detector output representing the detected affected electromagnetic radiation including using the measured power of the emitted electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Described herein is a method for identifying or verifying or otherwise characterising a liquid based drug sample comprising: emitting electromagnetic radiation in at least one beam at a sample, the electromagnetic radiation comprising at least two different wavelengths and measuring the power of the emitted electromagnetic radiation, detecting affected electromagnetic radiation resulting from the emitted electromagnetic radiation affected by the sample and providing output representing the detected affected radiation, and identifying or verifying the sample from the output representing detected affected electromagnetic radiation including using the measured power of the emitted electromagnetic radiation, wherein each wavelength or at least two of the wavelengths is between substantially 1300 nm and 2000 nm.

Described herein is a analyser for identifying or verifying or otherwise characterising a sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample, and a processor for identifying or verifying the sample from the detected affected electromagnetic radiation, wherein each wavelength or at least two of the wavelengths is between substantially 1300 nm and 2000 nm.

Preferably the source is a plurality of lasers in a single package, each laser configured to emit an electromagnetic radiation beam at a fixed or tuneable wavelength.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7). The term "comprising" as used in this specification means "consisting at least in part of". Related terms such as "comprise" and "comprised" are to be interpreted in the same manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

Preferred embodiments of the invention will be described with reference to the following drawings, of which:

FIG. 15 shows a matrix indicating verification for a set of sample drugs.

DETAILED DESCRIPTION

Overview

Figure 1:
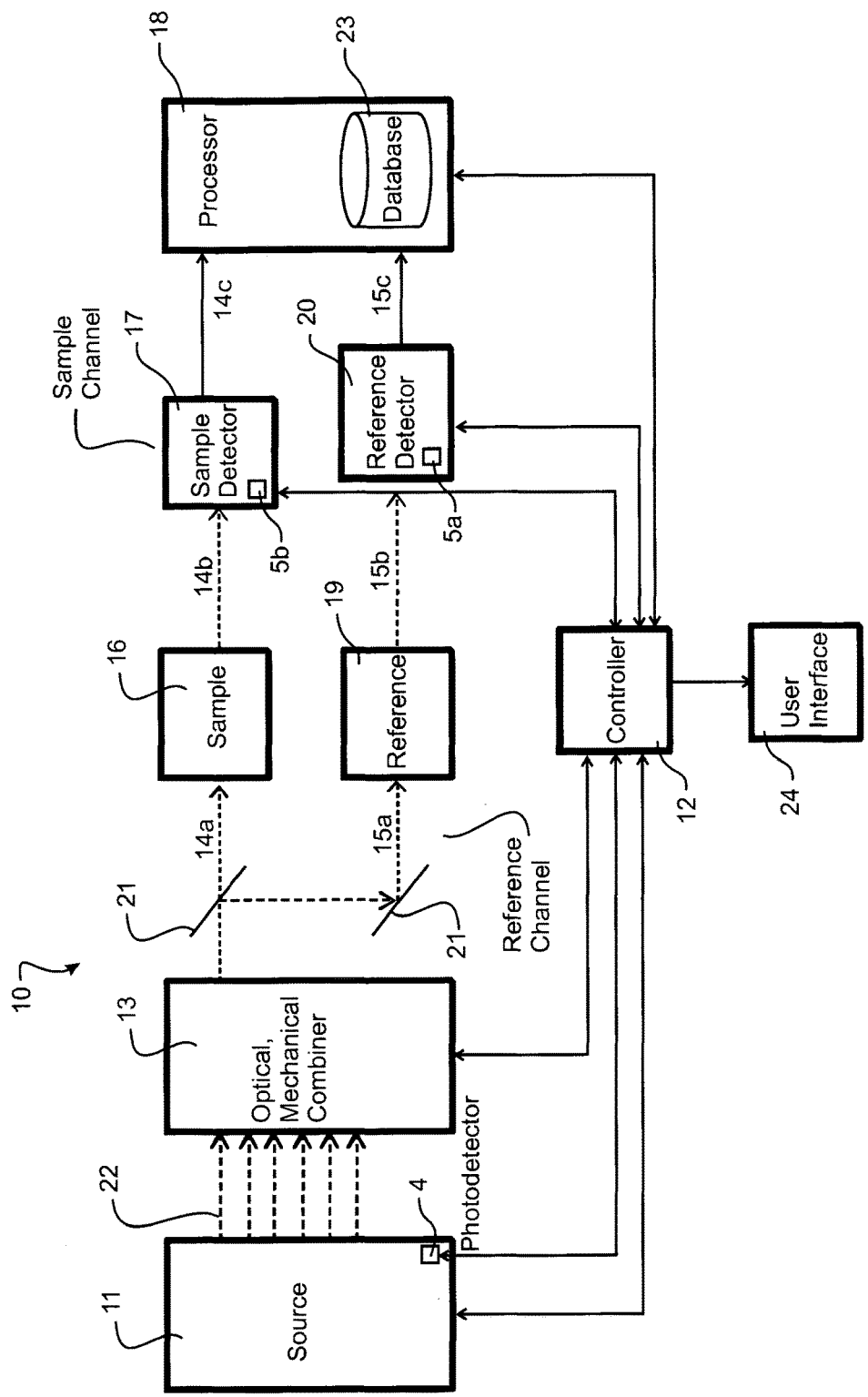
FIG. 1 shows in schematic form a spectroscopic analyser according to the present invention.

FIG. 1 shows an overview of a spectroscopic analyser 10 (for example, a spectrophotometer) according to the present invention for verifying or identifying (that is, analyse/characterise) drugs or other samples (e.g. blood, biological samples etc.). The term "drug" should be interpreted broadly to cover any pharmaceutical or other medicament or substance for treating patients, which is clinician controlled 9 (e.g. through a hospital, prescription or pharmacy) or freely available. The analyser (apparatus) 10 comprises a controller 12 that controls both physical control and processing aspects of operation. The analyser 10 comprises an electromagnetic radiation source 11 for generating and emitting electromagnetic radiation 22 with/at a plurality of wavelengths within a wavelength range. The source might also have a photodetector 4 or similar for control purposes. The electromagnetic radiation could take the form of a plurality of electromagnetic radiation beams at different wavelengths, or a single electromagnetic radiation beam comprising a plurality of wavelength components.

The term "wavelength" used for electromagnetic radiation output refers to a particular wavelength, such as 1300 nm. As will be appreciated, in practice, a source will not provide electromagnetic radiation output with a pure single wavelength—the output could contain components either side of the centre wavelength/peak. In this case, the term "wavelength" refers to the centre wavelength/peak of the electromagnetic radiation output, where the radiation output might also have a wavelength components either side of the centre wavelength, e.g. +/−30 nm, or +/−12 nm or even just a few nm (e.g. 2 nm for lasers) either side. Each such wavelength could be termed a "discrete" wavelength, as for practical purposes it is discrete, even if other components exist.

The electromagnetic radiation beams 22 could be visible light beams emitted from one or more lasers, for example. In one example, the electromagnetic radiation source ("source") 11 could be a single device that can be configured to generate and emit a plurality of electromagnetic radiation beams with different wavelengths in sequence or simultaneously, or that emits a single electromagnetic radiation beam with multiple wavelength components. In another example, the source 11 could be a set of individual sources, each configured to generate and emit electromagnetic radiation beams 22 with a desired wavelength. The term "source" can refer to a single source or multiple sources making up a source. In each case, the source 11 might generate a fixed wavelength electromagnetic radiation beam(s), or it might be tuneable to emit an electromagnetic radiation beam(s) at one of a range of wavelengths. Other examples could be envisaged by those skilled in the art also.

Preferably, the source 11 is configured so that each electromagnetic radiation beam 22 with a corresponding wavelength(s) can be independently emitted in sequence. This might be achieved through using a single source that is tuned to emit electromagnetic radiation beams that sweep through a range of wavelengths. Alternatively, where a source comprises multiple electromagnetic radiation sources, each of which can be operated in turn, it might be achieved by each source becoming the "active" source. So that the electromagnetic radiation beam of the active source is directed along the desired sample path 14a, each electromagnetic radiation beam output from the source can be arranged to hit a grating, mirror, prism or other optical apparatus 13 that redirects the beam from that source along the desired sample path 14a. In such arrangement, each electromagnetic radiation beam can be directed in sequence along the desired path as it is generated/activated. Alternatively, multiple electromagnetic radiation beams could be simultaneously directed along a beam path 14a, resulting in a single beam of electromagnetic radiation comprising a plurality of wavelength components. Alternatively, the sources could be arranged on a carousel or linear carriage (also represented by 13) that can be mechanically controlled to physically position each source to emit a radiation beam along the path 14a. These alternatives will be described further later. Other arrangements for redirecting a plurality of electromagnetic radiation beams from a source 11 along a desired path 14a could also be envisaged. The electromagnetic radiation beam directed along the path 14a can be termed the sample electromagnetic radiation beam.

The apparatus 10 comprises a sample/sample retainer 16 for holding a sample in the path 14a of the sample electromagnetic radiation beam. The sample retainer 16 could be a test-tube/test-tube holder, other type of test cell, part of an infusion pump/IV set, flow-cell, or any other type of device for holding any of these or holding a sample/substance in any manner. The sample could alternatively simply be placed in the path 14a. Any sample retainer allows for transmission of the electromagnetic radiation 22 to and through the sample. The sample is preferably a liquid based drug. The liquid based sample could, for example be a water based drug, but it could also be another type of sample/substance in water or other liquid carrier. The term "sample" is used generally to indicate a substance for analysis (e.g. verification/identification) and is not necessarily restricted to a test sample/small portion of a larger amount of substance. For example, the sample could be an actual drug to be administered—not simply a (sample) portion of that drug to be administered. The apparatus 10 can be used in a clinical or other environment to verify/identify a drug prior to admission. In this case, the sample put in the apparatus 10 will be the actual drug being administered.

An electromagnetic radiation beam emitted along the path 14a provides incident electromagnetic radiation on a sample (substance) 16 placed in the path (e.g. in the sample retainer.) Any incident electromagnetic radiation beam 14a that reaches the sample 16 is affected by the sample (e.g. either by transmission through and/or reflection by the sample.) The affected (sample) electromagnetic radiation 14b that exits the sample 16 is affected electromagnetic radiation and contains spectral information regarding the sample. For example, the affected electromagnetic radiation 14b comprises information about the intensity of the affected electromagnetic radiation at one wavelength of the incident radiation.

A sample detector 17 is placed in the affected electromagnetic radiation path 14b such that affected electromagnetic radiation 14b exiting the sample can be detected. The detector 17 can comprise, for example, one or more photo-detectors. The detector 17 outputs information 14c in the form of data/a signal that represents or indicates spectral information of the sample 16—that is, the output represents the detected affected electromagnetic radiation. The detector 17 output is passed through to a processor 18 that carries out optionally a pre-processing and a verification/identification algorithm in order to verify or identify or otherwise analyse the sample in the retainer. The processor 18 can fond part of the controller 12, or can be separate thereto. The processor 18 comprises or has access to a database 23 with reference/comparison data for verifying or identifying or otherwise analysing the sample. The path 14a, 14b, emitted and affected radiation and/or the sample/sample holder 16 can be termed the "sample channel." The sample detector 16 and inputs to the processor 18 (and optionally the processor itself) can also form part of the sample channel.

Optionally there might also be a reference channel, in which the emitted electromagnetic radiation beam 14a incident on the sample 16 is split 21 or otherwise redirected along a reference path 15a towards another retainer 19 containing a reference sample/substance (or simply "reference") 19. A beam splitter 21 could be used to achieve this. The reference could be saline, for example. The reference sample retainer 19 could be any one of those retainers 16 mentioned with respect to the sample channel. The reference electromagnetic radiation beam along the reference path 15a is incident on and affected by the reference sample 19 to produce affected (reference) electromagnetic radiation 15b which is incident on and detected by a reference detector 20. The reference detector 20 could be the same or different detector to that of the sample channel. In FIG. 1, the reference detector 20 is shown as an independent detector by way of example.

The reference detector 20 outputs information 15c in the form of data/a signal that represents or indicates spectral information 15c of the reference—that is, the output represents the detected affected electromagnetic radiation. The detector output 15c is passed through to the processor 18 that carries out pre-processing and a verification/identification algorithm in order to verify or identify the sample 16 in the retainer. The detector output 15c from the reference channel provides data from which to normalise and/or correct the sample channel data 14c. The reference channel might also comprises a neutral density filter prior to the sample. This attenuates the incident electromagnetic radiation in a manner to normalise the detected affected electromagnetic radiation, or otherwise modify it so that the output of the detector is at a suitable level to enable processing/comparison with the output of the detector on the sample channel.

Each electromagnetic radiation beam 22 has a wavelength (or has a plurality of wavelength components) that falls in the analysis range ("analysis region"), preferably of 1300-2000 nanometres (nm). This region can nominally be termed "near infrared" or "NIR". This region provides useful spectral information for verifying or identifying drugs. The wavelength of each electromagnetic radiation beam 22 (or the wavelengths making up an electromagnetic beam) is selected based on spectral characteristics (features) of the base liquid of the drug sample that fall within the analysis range. Such characteristics could be, for example, peaks, troughs, points of inflection, stable point or regions, plateaus, knees and/or slopes of that base liquid spectrum. Each wavelength selected is in the vicinity of (or within a region spanning) such a spectral characteristic. The position of a spectral characteristic could be defined by a nominal wavelength (of for example the centre wavelength of the characteristic) or a range of wavelengths defining a region spanning the characteristic.

Figure 2:
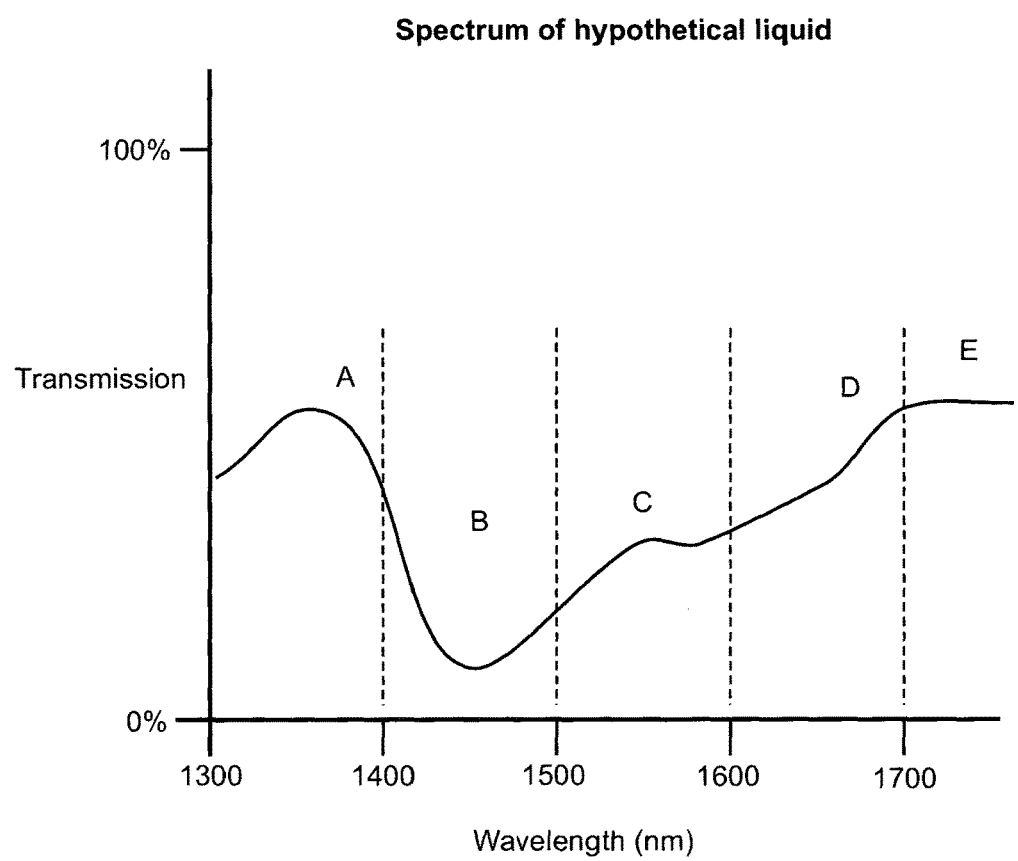
FIG. 2 shows in schematic form the hypothetical spectrum of a hypothetical liquid base/carrier.

Selection of each wavelength can be demonstrated with reference to the spectrum of a hypothetical base liquid as shown in FIG. 2. The hypothetical spectrum comprises the following spectral characteristics A-E in the analysis range.

A peak between 1300 nm and 1400 nm (centre wavelength of 1350 nm of actual peak) (A).
A trough between 1400 nm and 1500 nm (centre wavelength of 1450 nm of actual trough) (B).
An inflection between 1500 nm and 1600 nm (centre wavelength of 1550 of actual inflection) (C).
A slope between 1600 nm and 1800 nm (D).
A plateau between 1800 nm and 2000 nm (E).
A knee is also shown around 1800 nm between characteristics D and E.

For analysis of drugs with this hypothetical liquid as a base, wavelengths could be chosen that are within the vicinity of the wavelength ranges (or centre wavelength) for one or more of the spectral features A-E above, or that fall within in a region spanning (defining/delimiting) the wavelength ranges for one or more of the spectral features A-E above. A wavelength in the "vicinity" of a spectral characteristic also can mean a wavelength at the spectral characteristic centre wavelength. For example, three different wavelengths could be chosen as follows.

Wavelength #1 1310 nm—within the region 1300-1400 nm for feature A.
Wavelength #2 1450 nm, roughly at or within the vicinity of the centre wavelength of feature B.
Wavelength #3 1800 nm, at the edge/knee (i.e. within the region) of feature E.

The chosen discrete wavelengths that relate to spectral characteristics of the liquid spectrum can be termed "selected wavelengths" or "chosen wavelengths". In general terms, the selected or chosen wavelengths "correspond" to or "capture" a spectral characteristic.

It will be appreciated that FIG. 2 shows just some hypothetical examples of spectral characteristics (features)—many more are possible for a spectrum. Further, the wavelength ranges for spectral characteristics could overlap or even coincide. Further, a separate wavelength need not be chosen for each spectral characteristic in the analysis range—just a selection of wavelengths relating to a selection of spectral characteristics might be chosen. It might not be possible to define a spectral characteristic by a wavelength range, or any such range might vary depending on interpretation. A wavelength in the vicinity of a spectral characteristic might instead be chosen. This could be a wavelength that is near or within a certain tolerance (e.g. +/−30 nm) of the centre point wavelength of a spectral characteristic, for example.

In addition, the selected wavelength might be influenced by sources 11 that are readily obtainable or configurable to a wavelength that is in the vicinity of or falls within in a region spanning such a spectral characteristic. The selection of suitable wavelengths for the emitted radiation will provide better information for accurate verification or identification by the processor.

In addition, preferably, the selected wavelengths can be selected independently from the drug(s) being tested.

Figure 3:
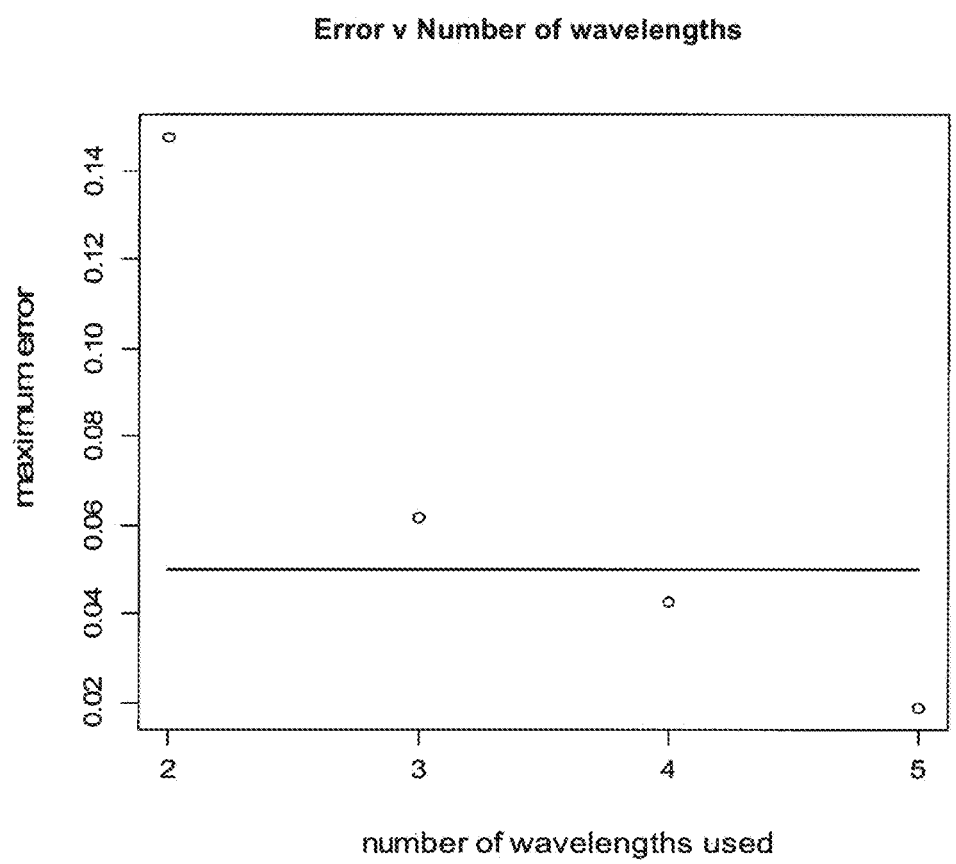
FIG. 3 is a graph showing the error vs. number of wavelengths used in the spectroscopic analyser.

Any suitable number of wavelengths can be used. Optionally, although not essentially, the number of different wavelengths constituting the electromagnetic radiation (either in one or multiple beams 22) provided by the source 11 is at least $\log_2 n$, where n is the number of samples that are tested for. The more wavelengths that are used, the better the accuracy, but this is optimised against costs and convenience. As seen in FIG. 3, as the number of electromagnetic radiation beams/wavelengths increases, the error of detection decreases. A selection of two wavelengths provides an error of 0.14 for a set of 30 drugs, whereas five wavelengths provide an error of just 0.02.

One of the electromagnetic radiation wavelengths 22 can be selected to have a wavelength at an anchor point, which can be used to eliminate the need for a reference channel. The anchor point is chosen to have a wavelength in a stable or other suitable portion of the spectrum of the underlying base liquid. The anchor wavelength is described further later.

Upon receiving output from a sample detector 17 and optionally a reference detector 20, the processor 18 executes an algorithm that accesses a database 23 comprising comparison data, and uses that output to verify or identify the sample 16 based on the affected electromagnetic radiation 14b detected from the sample 16, and optionally where a reference channel is used, the detected affected radiation 15b from that reference sample using the comparison data. The processor 18 can operate with or independently from the controller 12. Processing will be described further later.

A user interface 24 allows a user to operate the apparatus 10, including setting parameters, inputting anticipated drugs and receiving the results of analysis (via a screen, display, audio alarm, indicator or similar). The results might indicate whether the drug is as anticipated (verification/confirmation), or might advise of the drug (identification).

Preferably, the apparatus 10 also comprises a feedback system to stabilise the temperature of the electromagnetic radiation source 11 and/or the detectors(s) 17, 20. In one example, thermistors detect the temperature of the electromagnetic radiation source and/or detector(s). Peltier cooling devices can be operated to cool and stabilise the temperate of the source 11 and detectors 17, 20. The output of the thermistor(s) is sent to the controller 12, which controls the peltier cooling devices to cool the source and/or detectors. Preferably the thermistor is the built-in photodetector thermistor 5a, 5b. And the peltier thermo-electric cooler is built-in to the photodetector 5a, 5b.

The apparatus 10 works generally as follows, with reference to the flow diagram in FIG. 4. The controller 12 is used to operate the source 11 to emit one or more electromagnetic radiation beams 22 (preferably individually and in sequence) with/at the selected wavelengths towards the sample 16, step 40. The electromagnetic radiation incident 14a on a sample 16 is transmitted or reflected through the sample and becomes affected electromagnetic radiation 14b which is detected by the detector 17, step 41. Optionally, the emitted radiation maybe diverted by a beam splitter 21 also to a reference sample 19, which is detected by the same or a different detector 20, step 42. The outputs 14c, 15c from the sample detector 17 and optionally the reference detector 20 are passed to the processor 18, step 42. Here pre-processing takes place to normalise and/or correct the detector output 14c, 15c, step 42. Then the identification/verification algorithm is executed, step 43, which includes querying the database 23 of reference drugs, the information from which being utilised to identify or verify the sample from the normalised detector output. The result of the verification or identification of the sample is communicated by the user interface 24, step 44.

Other options will become apparent as a more detailed description of the invention is provided.

First Embodiment

One possible embodiment of the invention will now be described in detail by way of example. This should not be considered limiting but illustrative. The embodiment is described in relation to an apparatus for providing verification or identification of water based drugs from e.g. a set of 30 drugs.

Figure 5:
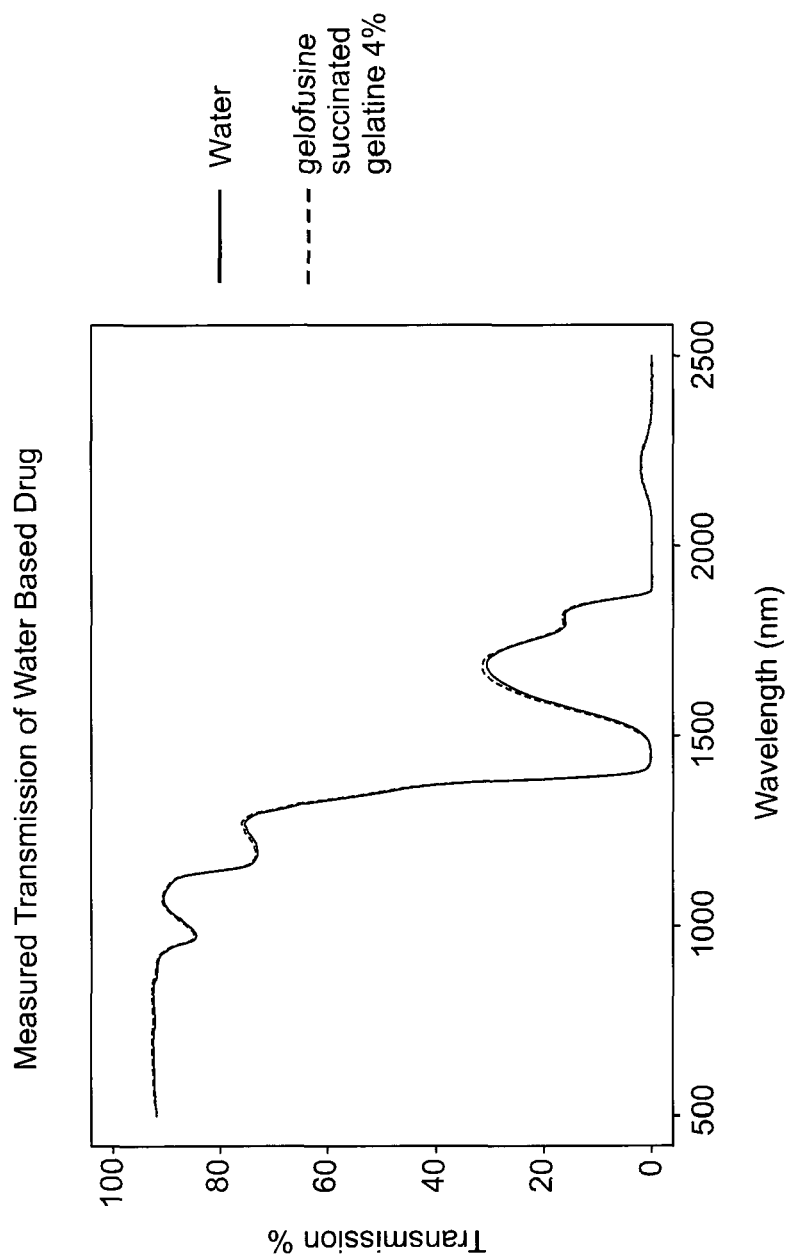
FIG. 5 shows the spectrum of a drug (gelofusine succinated gelatine solution 4%) overlaid the spectrum of a liquid based, being water.

Six wavelengths of electromagnetic radiation are chosen for this example, six being greater than $\log_2$ n of 30. The wavelengths are chosen in the analysis range and are based on the spectral characteristics of water, being the base liquid, falling in that range. The spectrum of a water based drug (or other liquid based drug or aqueous solution) will be heavily dominated by the base liquid spectrum. For example referring to FIG. 5, the spectrum (dotted line) of drug W (gelofusine succinated gelatine solution 4%) is very similar to the spectrum of water (solid line). This is because the spectrum of water dominates. However, the differences in transmission coefficient between different water based drugs can be measured. Focussing on areas/wavelengths of spectral characteristics of the water spectrum, by using electromagnetic radiation beams at those wavelengths, the difference between the water spectrum and the water based drug spectrum at those wavelengths can be utilised to provide drug discrimination for drug identification or verification.

Figure 6:
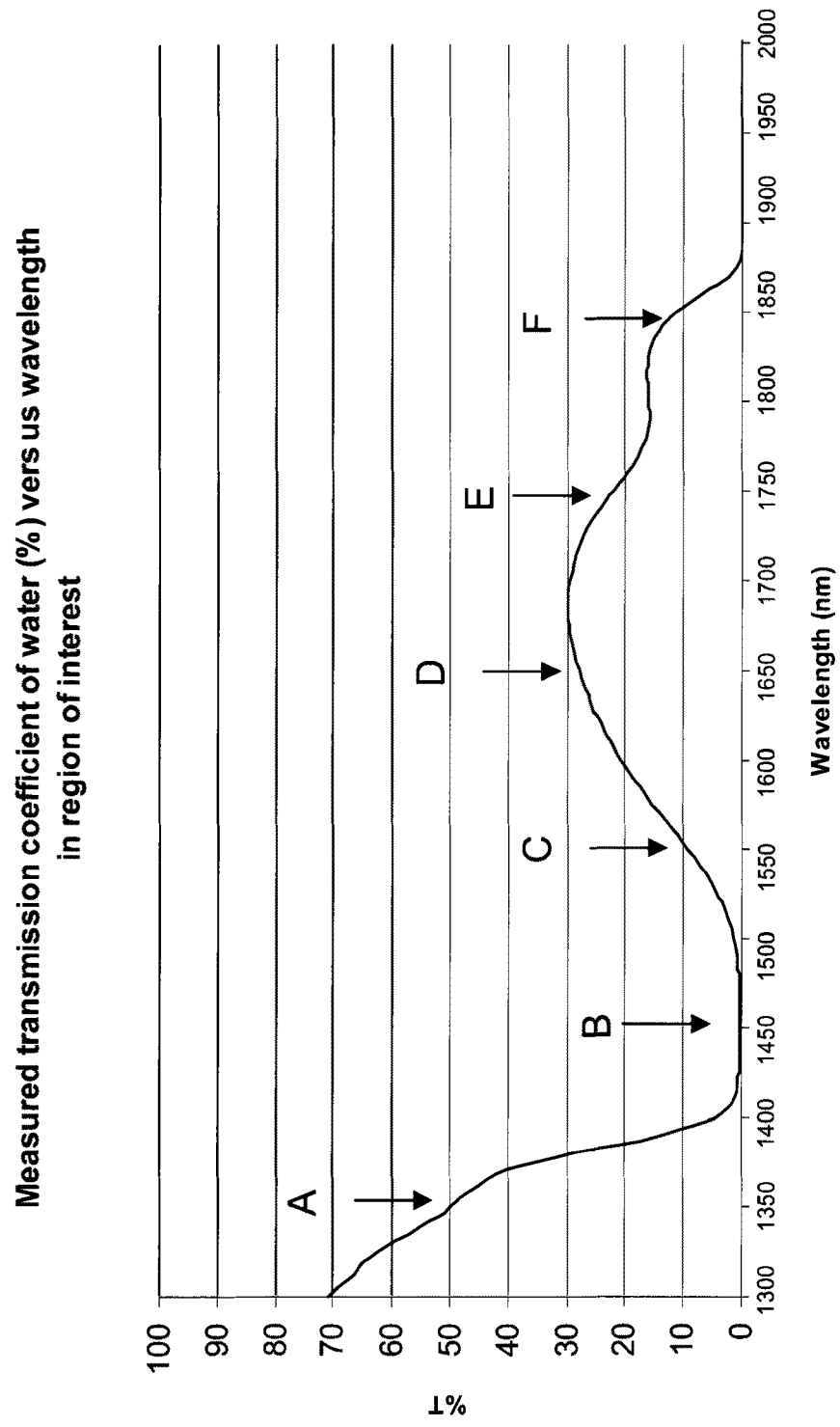
FIG. 6 shows spectral characteristics of water between 1300 and 2000 nm.

FIG. 6 shows a spectrum of water with some possible spectral characteristics (features) in the analysis range identified, and explained further below.

Spectral characteristic A (slope)—in a first region between 1300 nm and 1400 nm.

Spectral characteristic B (plateau/trough)—in a second region between 1400 nm and 1500 nm.

Spectral characteristic C (slope)—in a third region between 1500 nm and 1600 nm.

Spectral characteristic D (peak)—in a fourth region between 1600 nm and 1700 nm.

Spectral characteristic E (inflection)—in a fifth region between 1700 nm and 1800 nm.

Spectral characteristic F (knee) a sixth region between 1800 nm and 2000 nm.

This is not an exhaustive list of possible spectral features.

The selection of a wavelength for an electromagnetic radiation beam is not strictly fixed, and not necessarily solely based on spectral characteristics of the base liquid. It is influenced by the wavelength of spectral characteristics in spectrum of the base water of the drug sample, but in addition the selected wavelength can be based on other factors also. For example, in interest of cost effectiveness and a regularly obtainable supply chain, it might be preferable to use or select an alternative wavelength that is close to the spectral characteristic but not quite the same, if that alternative wavelength is easily obtainable by an off-the-shelf laser or other optical component.

For example, it is possible to use 1310 and 1550 nm as selected wavelengths for water based drugs as there are many devices configured for these wavelengths as they have wide spread use within the communications industry. Laser diodes nominally have centred wavelengths at 1650 nanometres, 1750 nanometres and 1850 nanometres, although these, can be varied by up to plus or minus 30 nanometres. So wavelengths in these ranges can also be selected. Therefore by looking at the availability of these components, and the spectral characteristics of the base liquid, suitable wavelengths for the emitted radiation can be determined.

Therefore, based on the above explanation, each of the six wavelengths can be chosen to be within the vicinity or within the region spanning one of each of the spectral features, but also influenced by the availability of hardware. The six wavelengths for water could therefore be (by way of example): 1350 nanometres corresponding to feature A, 1450 nanometres corresponding to feature B, 1550 nanometres corresponding to feature C, 1650 nanometres corresponding to feature D, 1750 nanometres corresponding to feature E and 1850 nanometres corresponding to feature F, all which fall within the 1300-2000 nanometres. As can be seen the 1350 nm to 1850 nm wavelength selections do not match exactly to peaks and troughs and other spectral characteristics in the water spectrum, although are close. The selections also relate to operating wavelengths of available hardware. These are of course nominal wavelengths and the actual wavelength might vary in practice due to source 11 characteristics.

Figure 7:
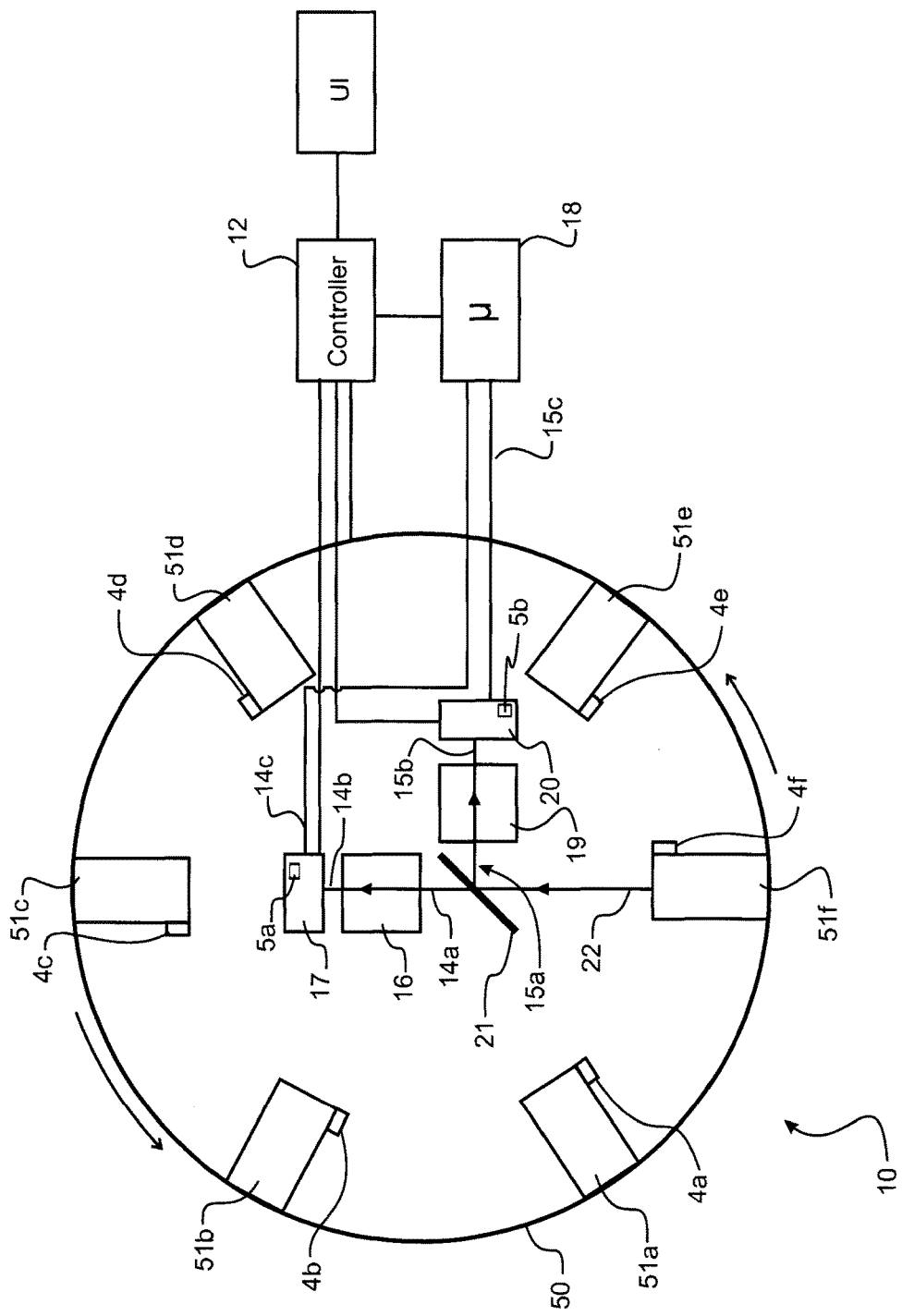
FIG. 7 shows a schematic diagram of a first embodiment of the spectroscopic analyser in which the sources are lasers on a rotating carousel.

FIG. 7 shows in schematic form one possible form of the apparatus 10 as generally described in FIG. 1. The spectroscopic analyser 10 has a controller 12 and a carousel 50 that supports six lasers 51a-51f, which together form the source 11 to output electromagnetic radiation 22 at a plurality of wavelengths in the form of light. Each laser is tuned or tuneable to emit electromagnetic radiation 22 at one of the six wavelengths defined above. Each laser can comprise or be formed from laser diodes providing a stable, high intensity, narrow band collimated electromagnetic radiation output that is readily controlled electronically via driver circuitry. Each laser comprises a lens that can collimate the emitted electromagnetic radiation 14a into a beam using appropriate lenses. Each laser 51a-51f can have one or more photodiodes 4a-4f for detecting output electromagnetic radiation for feedback control of that radiation. Lasers have fewer heat emission problems than other sources, thus reducing the detrimental effects of heat on the measurements. The output power of each laser preferably is nominally the same (typically 30 mW) in the interests of having a balanced apparatus. Preferably, this also enables a common diode driver circuit to be used for the laser diodes.

The controller 12 can control the carousel 50 to rotate about an axis to activate any one of the lasers 51a-51f in turn and align the activated laser (e.g. 51f as shown) to emit a beam 22 along the sample path/beam path 14a. The lasers 51a-51f can also be turned off completely to facilitate the measurement of dark current signals if required. The use of mechanically activated optical chopper can thereby be eliminated (although one can be included if desired.) Once activated, the laser emits electromagnetic radiation 22 towards the sample along the path 14a. The path 14a from the source to the detector is preferably predominantly via free-space preferably with minimal if any optical fibre components. This reduces optical attenuation and hardware. The apparatus also comprises a sample retainer 16a, which is aligned with the beam path 14a. The emitted electromagnetic radiation from an active laser 51a-51f is incident on and transmits or reflects through the sample 16 in the sample retainer.

The detector 16 is placed in the affected radiation path 14b that exits the sample 16a. Preferably the detector 16 is a single photodetector/photodiode biased to have a suitable response to detect electromagnetic radiation of wavelengths that will be in the affected radiation. A single detector reduces the errors due to variability introduced by components—it removes the relative differences between multiple photodetectors enabling a more stable response to the output of the emitted electromagnetic radiation thus enhancing sensitivity. An InGaAs photodiode could be used, for example. The detector 17 detects the affected radiation 14b and the output 14c of the detector 17 is passed to a processor 18 that verifies or identifies the sample as described above.

The apparatus also has a beam splitter 21 to redirect the incident electromagnetic radiation beam 22/14a towards a reference sample retainer along a reference path 15a, which passes through to a reference detector 20. The output of the reference detector 20 is also passed to the processor 18. The reference could be saline, for example.

Preferably, the apparatus also comprises a feedback system to stabilise the temperature of the electromagnetic radiation source 11 and the detectors(s). In one example, thermistors detect the temperature of the electromagnetic radiation source and/or detector(s). Peltier cooling devices can be operated to cool and stabilise the temperate of the source and detectors. The output of the thermistor(s) is sent to the controller, which controls the peltier cooling devices to cool the source and/or detectors. Preferably the thermistor is the built-in photodetector thermistor 5a, 5b. And the peltier thermo-electric cooler is built-in to the photodetector 5a, 5b.

Figure 4:
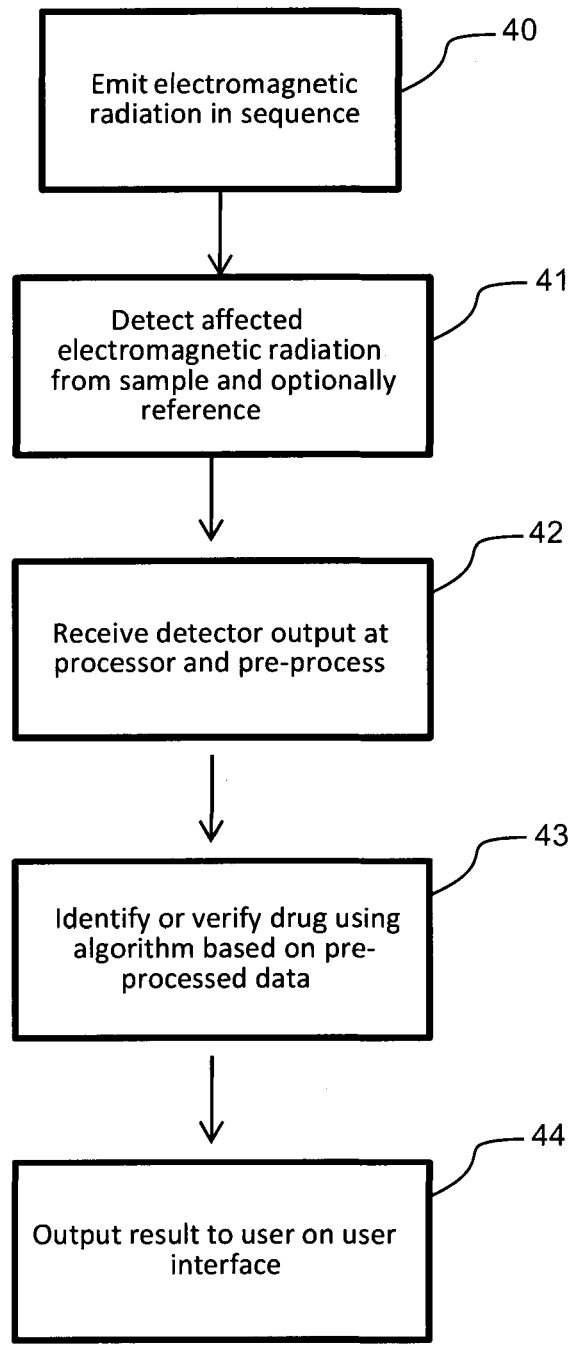
FIG. 4 is a flow diagram showing operation of the spectroscopic analyser.

Referring to FIG. 4, operation of the apparatus 10 will now be described. The controller 12 operates the carousel 50 to rotate each laser 51a-51f in turn to the activate position. When in the activate position, the laser 51a-51f is operated by the controller 12 to emit an electromagnetic radiation beam at one of the selected wavelengths to the sample 16 (and optionally to reference sample 19.) In this manner, six electromagnetic radiation beams with different selected wavelengths are emitted, step 40, in sequence from each of the six lasers 51a-51f, each tuned to a different selected wavelength. Each laser 51a-51f in turn emits an electromagnetic beam 22 along the path 14a towards the sample. The affected radiation coming from the sample is detected, step 41, for each electromagnetic radiation beam emitted 14a towards the sample 16. The electromagnetic radiation beam could be switched on and off to get a reading/measurement made by the detector during the off phase also—this can give a dark signal/current for reference purposes. The emitted electromagnetic radiation is also directed along the reference path 15a, through the reference sample 19 using the beam splitter 21, and detected by the reference detector 20. The outputs from the sample detector 17 and the reference detector 20 are passed to the processor 18, step 42. The processor (optionally) carries out pre-processing on the output from the detectors, and then verifies or identifies the drug based on the pre-processed outputs, step 43. It outputs the results via the user interface 24, step 44.

Figure 8:
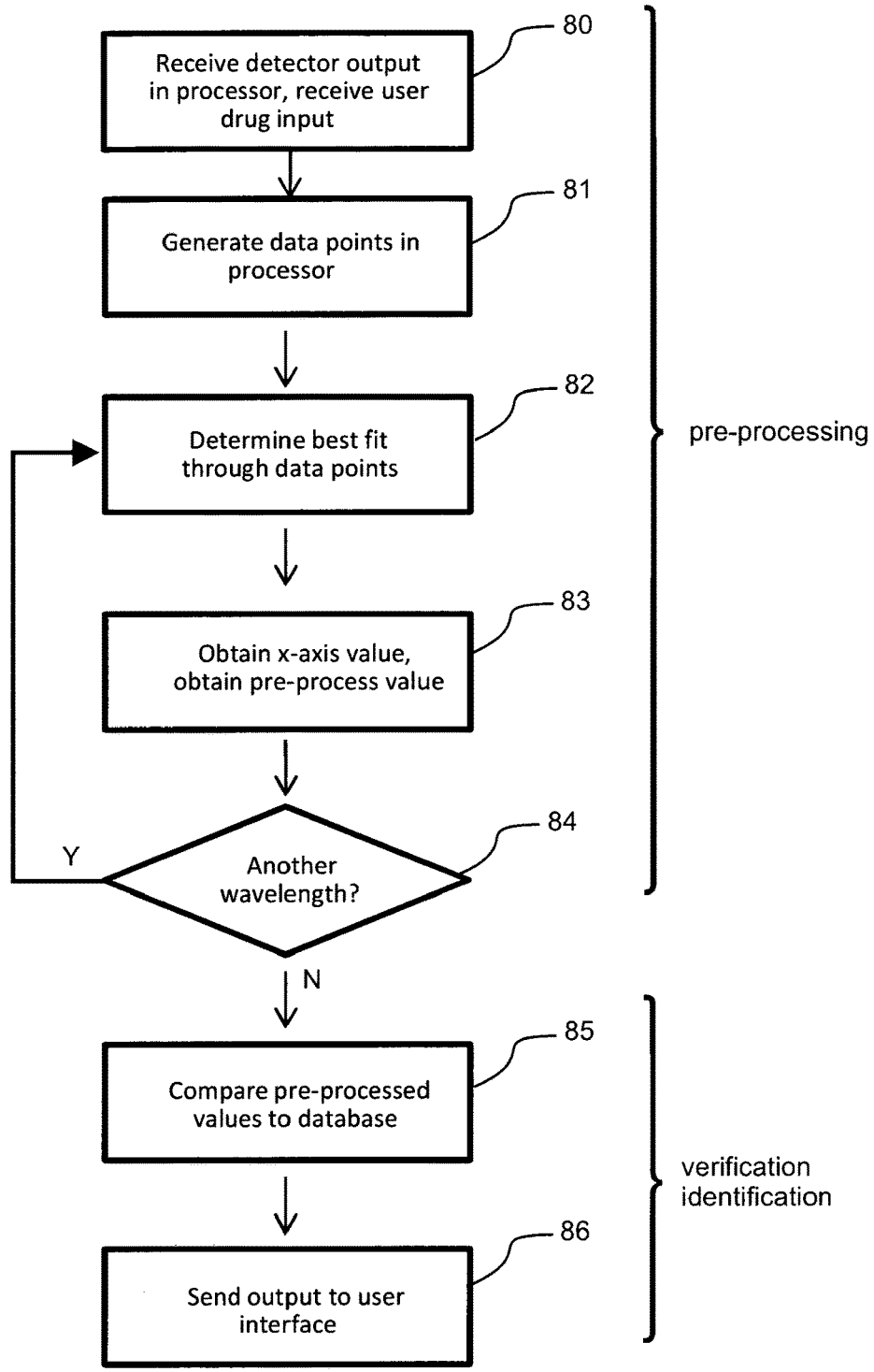
FIG. 8 shows a method of processing the output from the detectors, including a pre-processing and a verification/identification stage.

In one possible embodiment, the processor 18 comprises or implements a pre-processing method and then a verification/identification method as shown in FIG. 8. In this embodiment a reference channel is used and also dark current readings. Dark current is the output provided by the detectors 17, 20 when no electromagnetic radiation (e.g. light) is incident on them. This dark current reading from the detector can be subtracted from the actual reading from the detectors for calibration purposes. Having a dark reading is not essential for the invention and is described here as one possible option—the remaining description of the processing method would work also without dark readings being taken or by.

Figure 9:
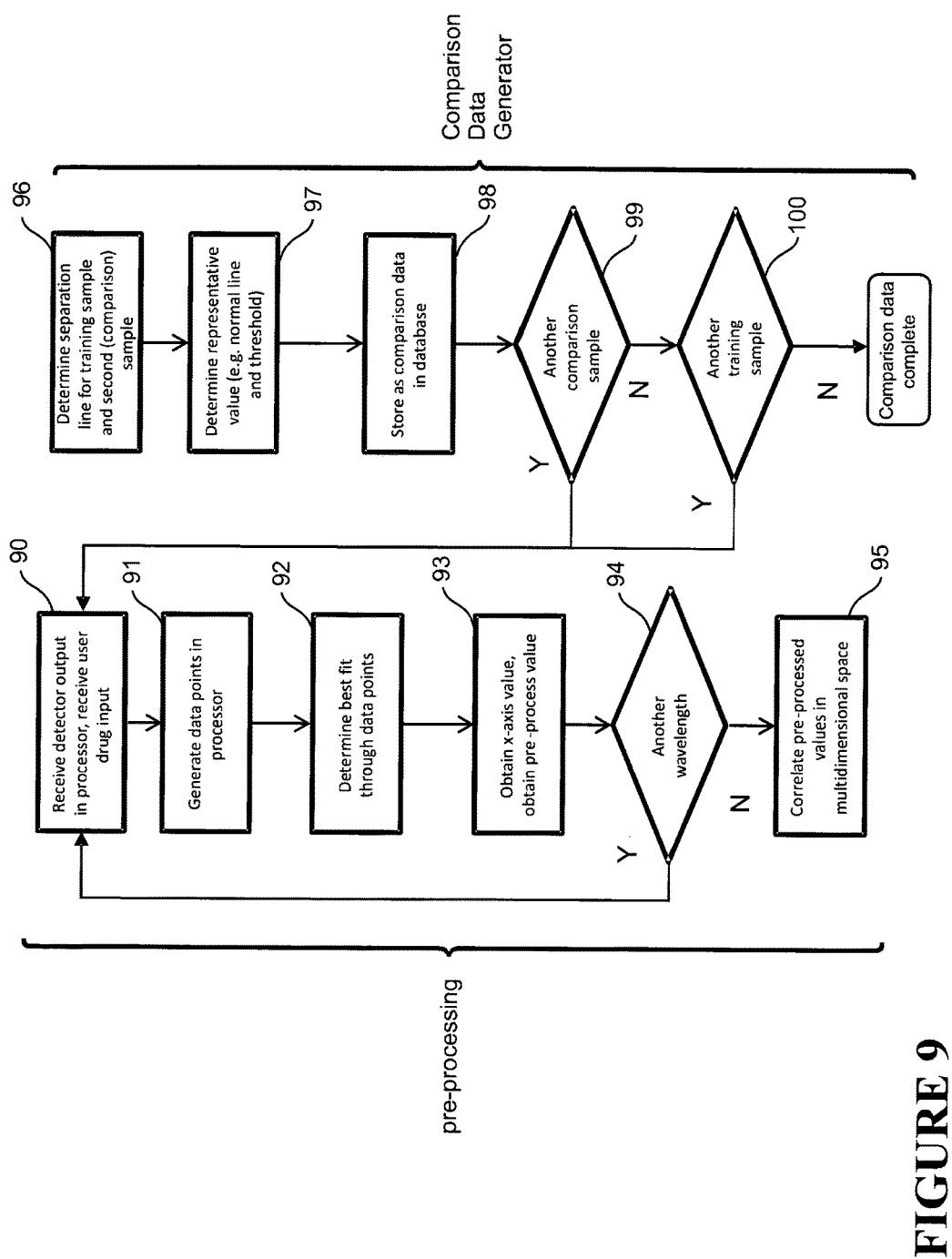
FIG. 9 shows a method of processing the output from the detectors, including a pre-processing and comparison data generation stage.
Figure 11:
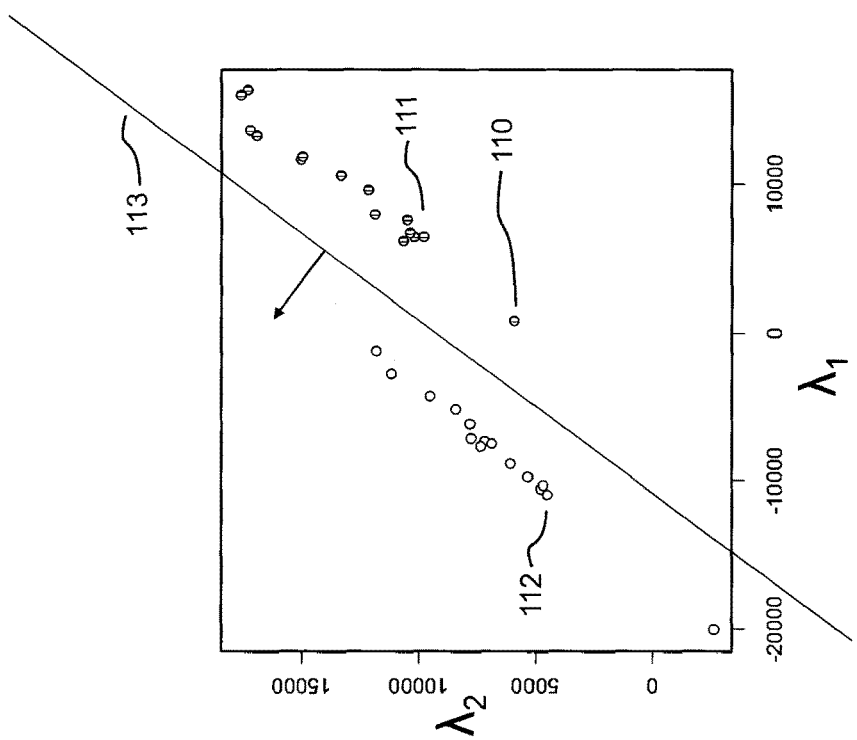
FIG. 11 shows a separation line between pre-processed data points for a training sample and a comparison sample.
Figure 10:
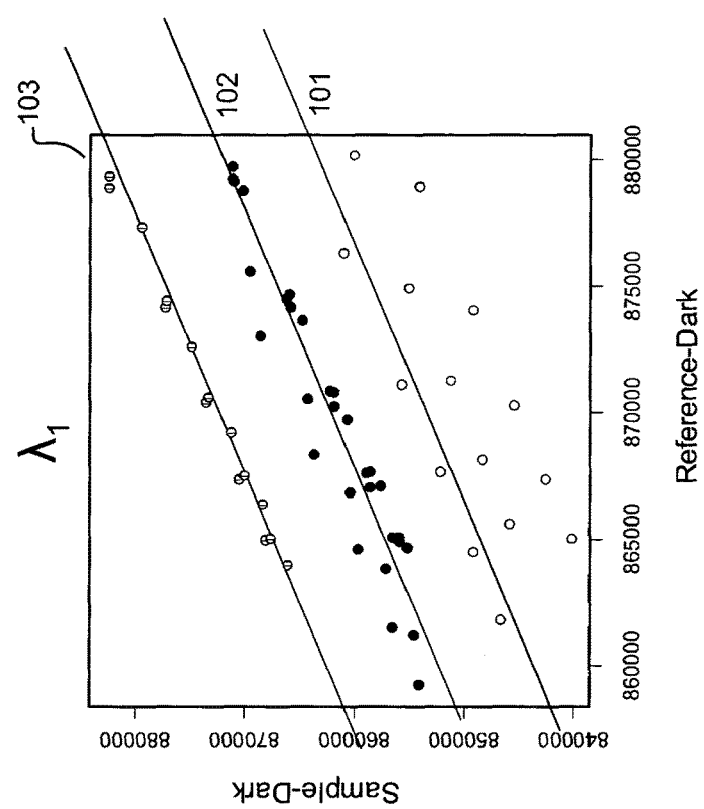
FIG. 10 shows a best fit line through data points obtained from outputs from the sample and reference detectors.

Prior to carrying out the verification or identification in FIG. 8, a training process is carried out to produce a comparison data from which samples can be verified/identified as shown in FIGS. 9-11. In the training process, an algorithm is used to generate the comparison data, which determines the particular linear combination of data values from each of the sample data that optimises the separation between different drugs. The resulting mathematical rule is then applied to the data acquired for the drug under test to verify that it is the intended drug. In the embodiment described, dark current readings are used. The training process preferably comprises a pre-processing stage, and a comparison data generation stage. Pre-processing is not essential, but improves performance.

Referring to FIG. 9, for the training process, a number of training samples are tested in the analyser in turn. Each training sample relates to a sample that will be test for during actual use of the analyser. For each training sample, output from both sample and reference channels is received at the processor, step 90. If dark current is being used, the output from each detector for the dark reading is subtracted from the output of the actual reading. The output 14c received at the processor 18 from the sample detector 17 indicates the intensity of the affected electromagnetic radiation 14b for each emitted electromagnetic radiation beam at the sample 16. It may, for example, comprise data which directly or indirectly indicates photocurrent of the detector and/or intensity of the detected electromagnetic radiation. Likewise, the output 15c received at the processor 18 from the reference detector 20 indicates the intensity of the affected electromagnetic radiation 15b for each emitted electromagnetic radiation beam at the reference sample. Preferably, the apparatus carries out multiple measurements for each wavelength. For example, at each wavelength, the apparatus detects affected electromagnetic radiation affected by the sample at 15 different times and passes this output to the processor, step 94. Similarly, at each wavelength, the apparatus detects affected electromagnetic radiation affected by the reference at 15 different times and passes this output to the processor, step 94.

Next, for each wavelength, the processor 18 generates from the output of the reference and sample detectors a range of sample data points for the sample that correlate an intensity of affected electromagnetic radiation 14b affected by the sample at a particular selected wavelength, step 91. These data points 100 could be plotted, as shown for example in FIG. 10—although it will be appreciated that the processor does not necessarily actually plot the data. The x axis shows intensity indicative values corresponding to detector output for the sample detector 17, and the y axis shows intensity indicative values correlating to detector output for the reference detector 20. The values indicate directly or indirectly the intensity of detected affected electromagnetic radiation. Where a reference channel is used, output on the reference detector is paired with output from the sample detector taken at the same time. Each sample/reference channel detector output value pair is plotted on the graph. Such measurements can be taken for several times for each wavelength. Therefore, the plot in FIG. 10 shows the values indicative of intensity 103 measured at several times (e.g. 15) for a particular selected wavelength (e.g. nominally 1350 nm) of electromagnetic radiation incident 14a on the training sample 16 and on the reference 19.

For each training sample, the process is then repeated to get similar data points for a second (comparison) sample 101 and a control (e.g. saline) 102. The sample/reference channel detector output value pairs for the second (comparison) 101 sample and control sample 102 could also plotted on the graph, as shown in FIG. 9, step 91.

A best fit straight line can then be calculated using a suitable statistical technique, step 92, and the intercept value of the x axis is found, step 92, for each of the:

training sample set, 103
second (comparison) sample 101, and the
control sample 102 set of data points for the particular wavelength (1350 nm), as shown in FIG. 10.

From this a normalised pre-processed value is found. For example, the x-axis intercept values (e.g. 842500 and 850500) for the training sample 103 and control 102 respectively can be found, and then can be subtracted from each other to obtain normalised pre-processed values (e.g. 8000), step 93. Similarly, the x-axis intercept values (e.g. 86000 and 850500) for the second (comparison) sample 101 and control 102 respectively can be found also, and then subtracted from each other to obtain normalised pre-processed values (e.g. 95000), step 93. This process can be carried out for each of the other selected wavelengths (e.g. five others in this case), step 94 and steps 90-93, resulting in a set of six normalised pre-processed values (—one for each wavelength) for the training sample. The process can also be carried out for each of the other selected wavelengths for the second (comparison) sample, resulting in a set of six normalised pre-processed values for the second (comparison) drug for each wavelength. These sets of normalised pre-processed values for the training sample and second (comparison) for each wavelength sample can be correlated/plotted in a multidimensional space, each axis corresponding to a wavelength and the pre-processed value for that wavelength being plotted relative to that axis.

In practice, this process, steps 90-94, can then be carried out numerous times for each wavelength, so that for each training sample and second (comparison) sample, there are a plurality of sets of six normalised pre-processed values. Each set can be plotted/correlated as one point in a multi-dimensional (six dimensions in this case) space. An example of such a plot is shown in FIG. 11. Here, for simplicity, only a two dimensional space is shown, each axis relating to the results from two wavelengths—in reality it would need to be a six-dimensional graph to cover all six wavelengths. For each set for each of the training sample and second (comparison) sample, a pair of two normalised pre-processed value (i.e. one value for each wavelength) is plotted as a single point on the two dimensional graph, e.g. 110, resulting in a normalised pre-processed value data set for the training sample 111 and the second (comparison) sample 112.

The pre-processing stage described above reduces the detrimental effects of systematic errors in the system and drift in the measured data. Note, the reference channel/value is optional. In an alternative, x-axis intercept values are found for the sample data only.

In an alternative embodiment, the pre-processing steps previously described can be omitted on the grounds that system drift and systematic errors can be virtually eliminated with the use of highly stable laser diode sources and a reference signal derived from the laser's own monitor diode output. This facilitates the use of a single channel with a single photo-detector eliminating the need for separate optical reference channel and/or control sample to be used. To this end, the data base of measured transmission spectra for a range of intravenous drugs can be built up in a more straightforward manner by sequentially measuring samples of each drug in a single channel using multiple test tubes.

After the data has been pre-processed for the training sample and second (comparison) sample and correlated as shown in FIG. 11, a representative value can be obtained for the training sample. If no pre-processing is carried out, the process proceeds to finding the representative value on non-pre-processed (raw) data. First a line 113 that separates the training sample data set 111 from the second (comparison) sample data set 112 is determined, step 95. Then the normal direction of the line is used as a weighting in a score to separate the training sample from the comparison sample. Also, a threshold is determined below which the training sample falls, step 96. The threshold and weighting score provide a representative value for comparison data to assist in verification/identification for that training sample. The representative value is stored as comparison data in a database 23 for the training sample, step 98.

The entire process is the repeated (step 99, and steps 90-98) for the same training sample against a third (comparison) sample to get a second representative value for storing as comparison data in the database 23 for the training sample. Then the process is repeated again (step 99, and steps 90-98) against a fourth and subsequent comparison samples to generated a third and subsequent representative values for storing as comparison data for the training sample. Together these form the representative values in the comparison database to identify/verify the training sample.

The entire process (step 100, step 90-99) is the repeated for each other training sample (in the set of n drugs) against multiple comparison samples, in order to obtain representative values for each additional training sample also.

It will be appreciated that in describing the training process steps 90-100, there has been reference to graphs and techniques. These are described for illustrative purposes. Any processor carrying out the training process to determine representative values might not actually produce such graphs or utilise such techniques to obtain the end result, but rather use other processing techniques that achieve the same result.

The above training process will generate comparison data for each training sample (in the set of n drugs) that can stored in the database 23 and can be used to identify or verify actual samples from the set under test. The comparison database 23 can be generated well in advance of actual sample testing, or can be generated soon before or even on-the-fly. The comparison data can be considered as a multidimensional verification/identification matrix based on the acquired multidimensional spectral data from the detectors. The comparison data can be used to verify or identify any of the drugs from any of the other drugs in the set of n drugs.

Referring back to FIG. 8, once a comparison database is produced and stored in the database 23, verification/identification of actual samples occurs as follows. Output from both sample and reference channels is received at the processor, step 80. If dark current is being used, the output from each detector for the dark reading is subtracted from the output of the actual reading. The output 14*c* received at the processor 18 from the sample detector 17 indicates the intensity of the affected electromagnetic radiation 14*b* for each emitted electromagnetic radiation beam at the sample 16. It may, for example, comprise data which directly or indirectly indicates photocurrent of the detector and/or intensity of the detected electromagnetic radiation. Likewise, the output 15*c* received at the processor 18 from the reference detector 20 indicates the intensity of the affected electromagnetic radiation 15*b* for each emitted electromagnetic radiation beam at the reference sample. Preferably, the apparatus carries out multiple measurements for each wavelength. For example, at each wavelength, the apparatus detects affected electromagnetic radiation affected by the sample at 15 different times and passes this output to the processor, step 80. Similarly, at each wavelength, the apparatus detects affected electromagnetic radiation affected by the reference at 15 different times and passes this output to the processor, step 80.

This output is then preferably pre-processed, steps 81-84, in the same manner as described above for the training process and with reference to FIGS. 9 to 11. That description need not be repeated here, but in summary, data points are generated, step 81, best fit lines found, step 82, and x-axis values are obtained which provide normalised pre-processed values, step 83. This is done for all wavelengths, step 84. Pre-processing is not essential, but can improve performance.

After this pre-processing is carried out for the affected radiation of each wavelength, steps 81-84, the identification/verification algorithm can then be invoked, step 85. Verification involves confirming that a sample drug is the drug that is expected. For example, a clinician can specify what they think the drug is (e.g. from the set of n drugs) through the user interface 24, e.g. step 80, then use the apparatus to confirm whether the drug in the retainer is actually that drug which is specified by the clinician. Identification involves determining what a drug actually is, without any suggestion from the clinician as to what the drug is. For verification/identification, the spectral data (that is, the pre-processed values) are compared against the comparison data in the database 23, step 85, to identify the drug, or verify whether it is the anticipated drug as specified by the clinician. Output is then provided to the user interface, step 86.

In one possible identification/verification algorithm, once the sample data is obtained and pre-processed, representative values are found for the sample, in the same manner that they were found during the training process as explained with reference to FIGS. 9 to 11. The representative values are found for the sample at each selected wavelength and with respect to each other comparison sample. The representative values are compared to the representative values in the comparison data. If there is sufficient similarity between the representative values found for the sample and the representative values in the comparison data corresponding to the same sample, then verification or identification is made. Sufficient similarity can be determined using any suitable statistical or other technique. For example, sufficient similarity might occur when some or all of the representative values match those in the verification matrix. In another example, this might occur when the sample falls below the threshold for each comparison sample. An alarm or output might be made via a user interface to advise the user of the result of the verification/identification.

FIG. 15 shows test data for a set of 30 drugs verified using the analyser. In the test, each drug was inserted in the analyser, and then systematically the analyser was configured to check if it was one of the 30 drugs. If an alarm was raised, this indicated the drug was not the one that was anticipated, and the alarm noted. Each drug was tested 15 times, in relation to each of the other drugs. So, for example, Metaraminol was put into the analyser and then the analyser was configured to check for Metaraminol. After 15 tests, the analyser did not once raise an alarm, indicating that the analyser did not detect Metaraminol as another drug. Keeping Metaraminol in the sample retainer, the analyser was then configured to check for Heparin. For each of 15 independent tests, the analyser raised an alarm, indicating it detected each time that the drug in the analyser (Metaraminol) was not the drug it was expecting (Heparin). The analyser was then reconfigured for each of the other drugs, and the test done 15 times for each, while Metaraminol was in the sample retainer. The same process was then repeated for every other drug being used as a sample, with the analyser systematically being re-configured to check for every other drug. Each time an alarm was raised (indicating the analyser did not consider the drug in the retainer was that being checked form), the alarm was noted. The table in FIG. 15 reflects the number of times an alarm was raised of each drug detection combination. The error rates are shown. The low error rates demonstrate a significant improvement in verification accuracy.

Second Embodiment

Figure 12:
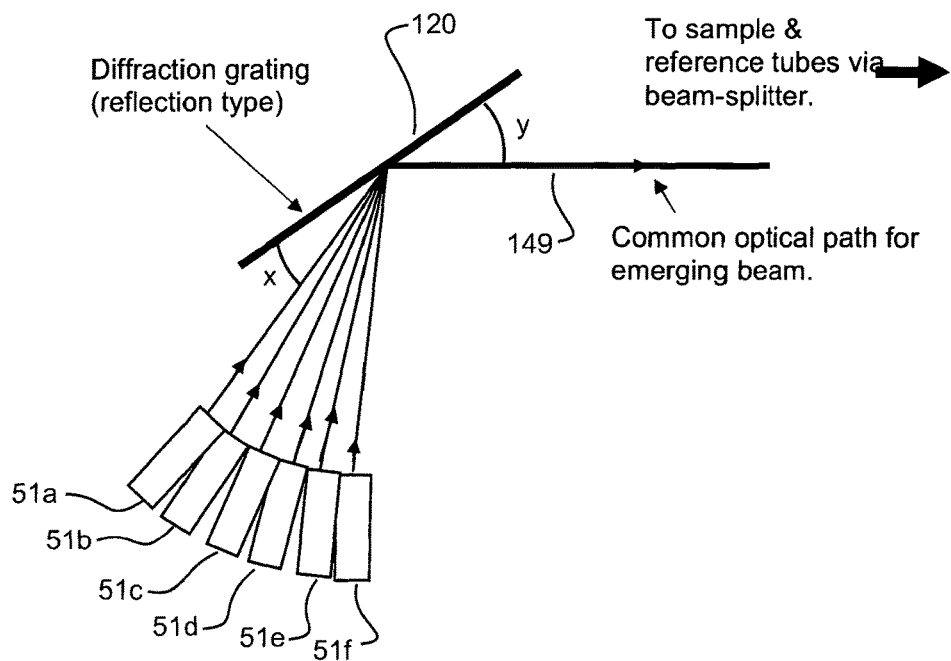
FIG. 12 shows a second embodiment in which the source comprises six lasers that are directed along the sample path 14a using a diffraction grating.
Figure 16:
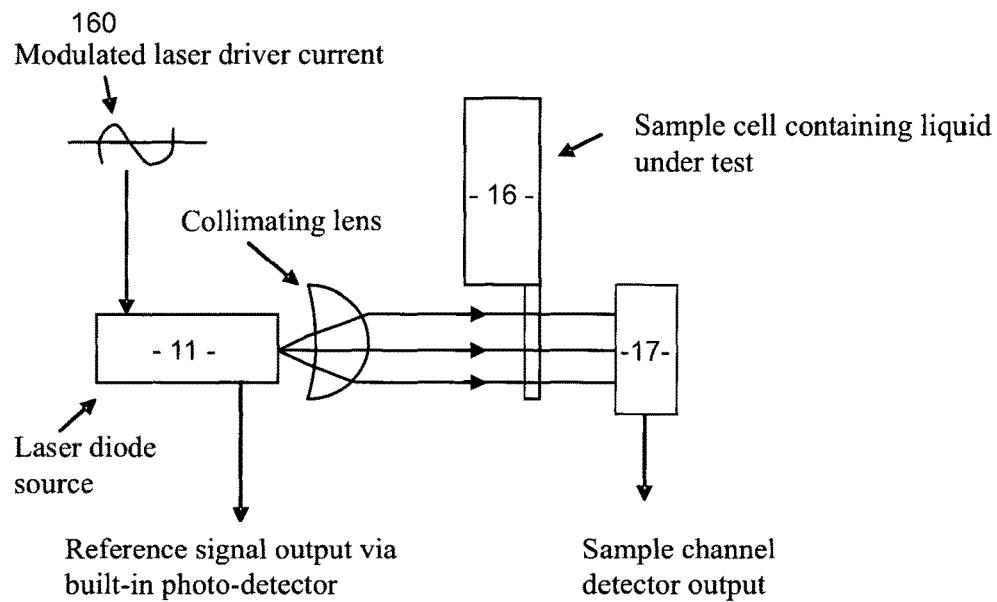
FIG. 16 shows an analyser using source modulation to eliminate a reference channel.

FIG. 12 shows an alternative embodiment of the apparatus 10. In this embodiment rather than using a carousel 50, the six lasers 51*a*-51*f* forming the source 11 are arranged to emit their electromagnetic radiation beam 22 towards a diffraction grating 120 of the reflection type. Each laser 51*a*-51*f* is operable to emit a tuned or tuneable wavelength of a collimated electromagnetic beam 22 towards the diffraction grating. The angle of incidence X on the grating surface for each laser 51*a*-51*f* is chosen that their first order diffracted beam emerges at the same angle Y thereby producing a common optical path 14*a* for each laser. The controller 12 activates each laser 51*a*-51*f* sequentially to emit a beam of a single wavelength towards the sample. Alternatively, multiple lasers 51*a*-51*f* could be operated at once such that an electromagnetic beam 22 comprising multiple wavelength components could be emitted towards the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Third Embodiment

Figure 13:
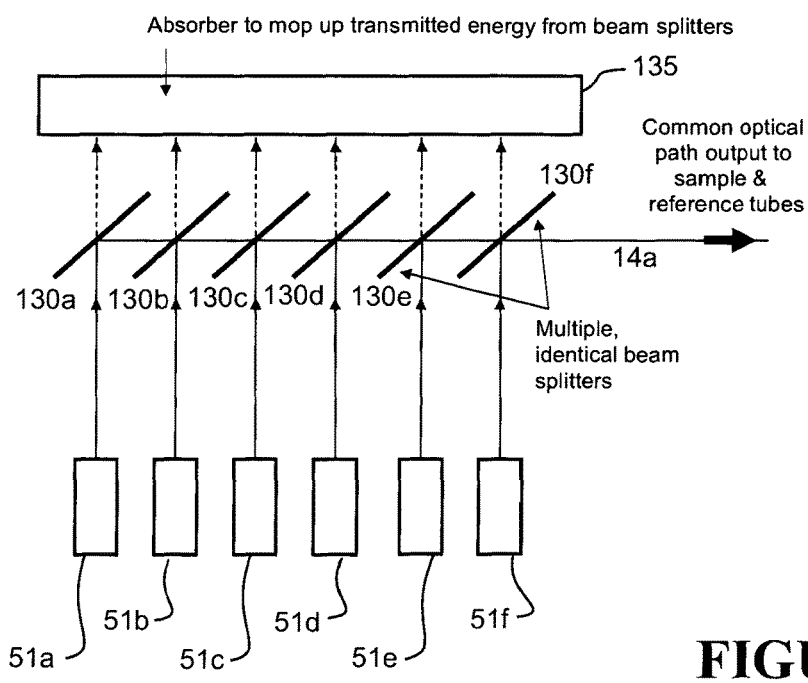
FIG. 13 shows a third embodiment comprising a source of six lasers the outputs of which are directed along a sample path using beam splitters.

FIG. 13 shows another alternative embodiment of the apparatus 10. In this embodiment rather than using a carousel 50, the six lasers 51*a*-51*f* forming the source 11 are arranged to emit their electromagnetic radiation beam 14*a* towards respective beam splitters 130*a*-130*f* that redirect the emitted electromagnetic radiation beam 22 along the sample path 14*a*. The controller 12 can control each electromagnetic radiation source 11 in turn to emit a tune or tuneable wavelength of electromagnetic radiation towards the sample via the respective beam splitter 130*a*-130*f*. Alternatively, two or more of the lasers 51*a*-51*f* could be activated at once to provide an electromagnetic beam 22 with multiple wavelength components towards 14*a* the sample 16. An absorber 135 is provided behind the beam splitter array to mop up transmitted energy from the beam splitters. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Fourth Embodiment

Figure 14:
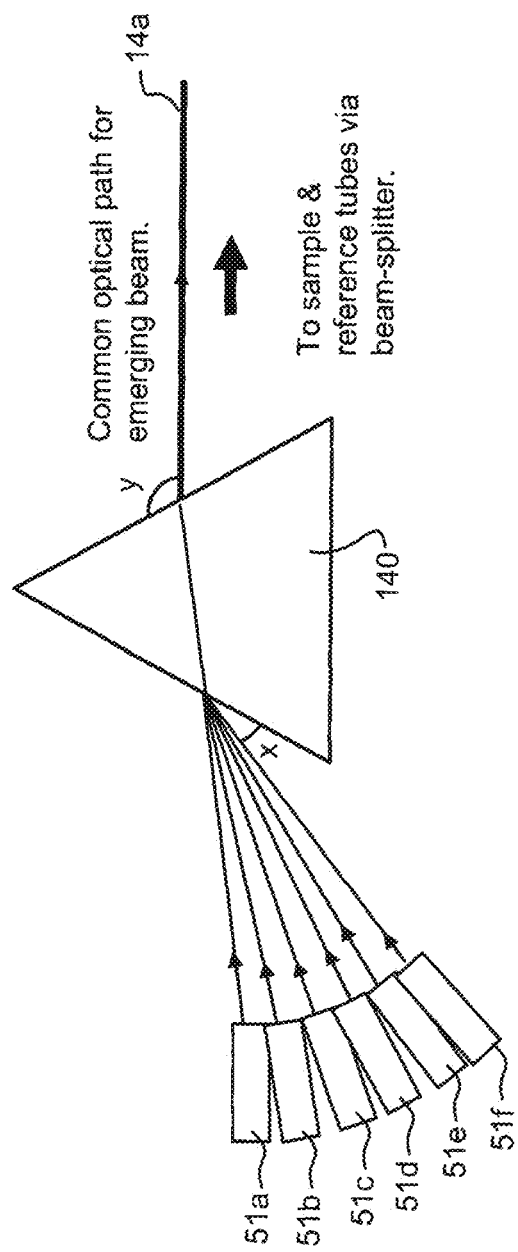
FIG. 14 shows in schematic form a fourth embodiment for the source comprising six lasers the outputs of which are converged onto a sample path using a prism.

FIG. 14 shows an alternative embodiment of the apparatus 10. In this embodiment rather than using a carousel 50, the six lasers 51a-51f forming the source 11 are arranged to emit their electromagnetic radiation beam 22 towards a prism 140. Each laser 51a-51f is operable to emit a tuned or tuneable wavelength of a collimated electromagnetic beam 14a towards the prism. The angle of incidence X on the grating surface for each laser 51a-51f is chosen that their first order refracted beam 22 emerges 14a at the same angle Y thereby producing a common optical path 14a for each laser 51a-51f. The controller 12 activates each laser 51a-51f sequentially to emit a beam of a single wavelength towards the sample. Alternatively, multiple lasers 51a-51f could be operated at once such that an electromagnetic beam 22 comprising multiple wavelength components could be emitted towards 14a the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Fifth Embodiment

Figure 20:
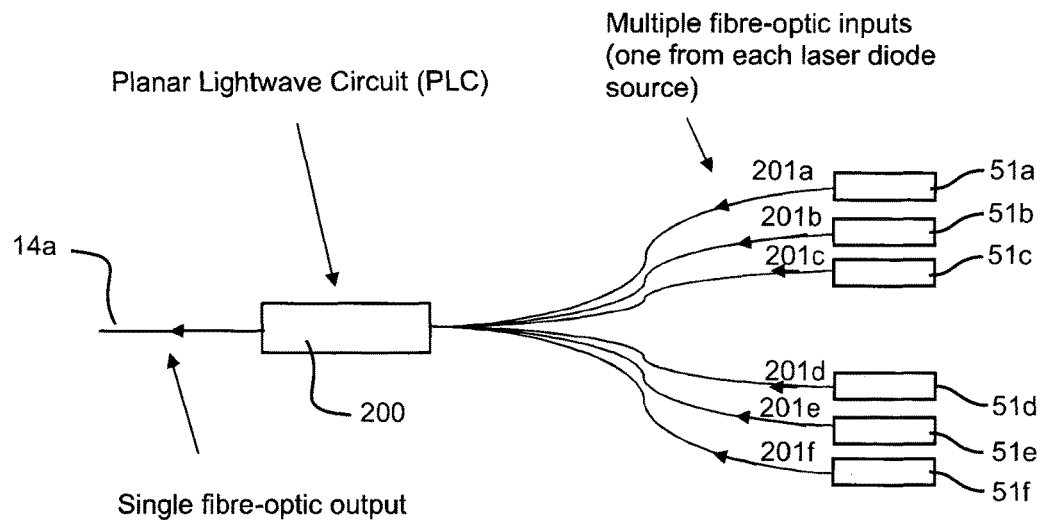
FIG. 20 shows in schematic form a fifth embodiment for the source comprising six lasers the outputs of which are converged onto a sample path using a planar lightwave circuit.

FIG. 20 shows an alternative embodiment of the apparatus 10. In this embodiment rather than using a carousel 50, the six lasers 51a-51f forming the source 11 are arranged to emit their electromagnetic radiation beam 22 through separate fibre optic cables 201a-201f towards a planar lightwave circuit (PLC) (fibre optic combiner) 200. Each laser 51a-51f is operable to emit a tuned or tuneable wavelength of a collimated electromagnetic beam 14a towards the PLC 200 via the fibre optic cables 201a-201f. The controller 12 activates each laser 51a-51f sequentially to emit a beam of a single wavelength towards the sample. Alternatively, multiple lasers 51a-51f could be operated at once such that an electromagnetic beam 22 comprising multiple wavelength components could be emitted towards 14a the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Sixth Embodiment

Figure 21:
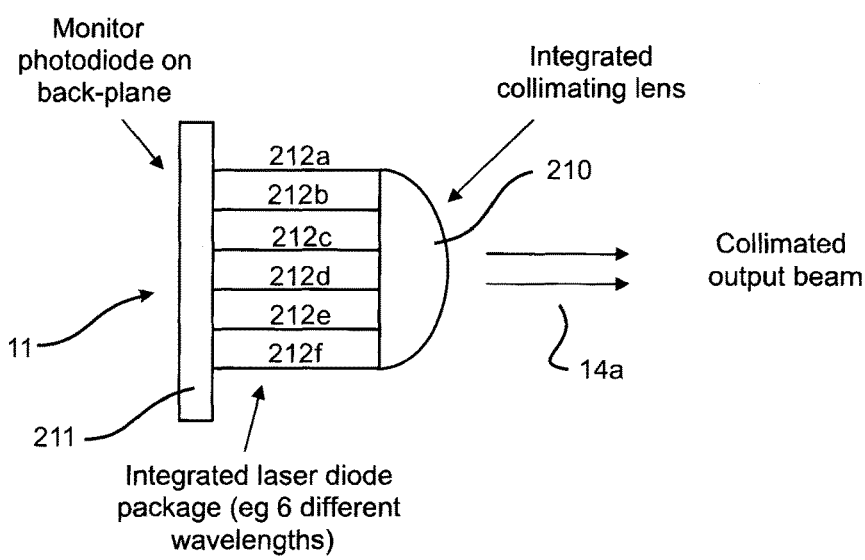
FIG. 21 shows in schematic form a sixth embodiment for the source comprising a single package source and collimated lens.

FIG. 21 shows an alternative embodiment of the apparatus 10. In this embodiment rather than using a carousel 50, a single package 211 comprising 6 lasers forming the source 11 are arranged to emit their electromagnetic radiation beam 201a-201f towards an integrated collimating lens 210. The laser is operable to emit a tuned or tuneable wavelength at each of 6 wavelengths towards the lens 210. The controller 12 activates the laser to sequentially to emit a beam 212a-212f of a single wavelength towards the sample. Alternatively, multiple beams 51a-51f could be operated at once such that an electromagnetic beam 22 comprising multiple wavelength components could be emitted towards 14a the sample 16 via the lens 210. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Alternative Embodiments

The nominal analysis range of 1300-2000 nm for selected wavelengths is chosen as it provides advantages for improved drug verification or identification. However, it will be appreciated that the reference to 1300-2000 nm should not be considered limiting, and wavelengths could be chosen that relate spectral characteristics in slightly different ranges or other ranges entirely. The selected wavelengths (and therefore the spectral characteristics) fall within any analysis range provide for improved identification/verification for drugs in the liquid carrier. For example, the analysis range could be a subset of 1300 nm-2000 nm, such as 1300 nm-1900 nm; 1350 nm-1950 nm; 1400 nm-1900 nm; 1500 nm-1800 nm or some other subset. The range could also be larger, such as 1250-2050 nm; 1200 nm-2100 nm; or 1150 nm-2150 nm or the like. The analysis range might even be offset from the nominal range, such as 1200 nm-1900 nm, or 1300 nm-1900 nm. These are non-limiting examples. In general, the analysis range could start, for example, anywhere from 1100 nm-1500 nm and end anywhere from 1800 nm-2150 nm. Even that is non-limiting and the range could be something different entirely that provides for improved verification/identification. Further, wavelengths falling outside these analysis ranges and corresponding to spectral features lying outside these analysis ranges above could also be used in combination with wavelengths falling in the analysis ranges mentioned. Using a plurality of wavelengths corresponding to spectral characteristics falling within the analysis range provides improved performance. Preferably any and all wavelengths are selected within the analysis range, but that does not preclude using wavelengths falling in other ranges also where that might be useful.

The range could be at least partially influenced by component selection. For example, silicon photodiodes have a response down to at least 1100 nm, so if used this wavelength might be used as the bottom end of the range. Preferably, the invention uses only one detector, so the range might be defined by what a single detector can cover—for example 1300 nm-2000 nm in the case of an InGaAs detector.

Other liquids to water might have other analysis ranges that provide improved identification/verification.

Figure 18:
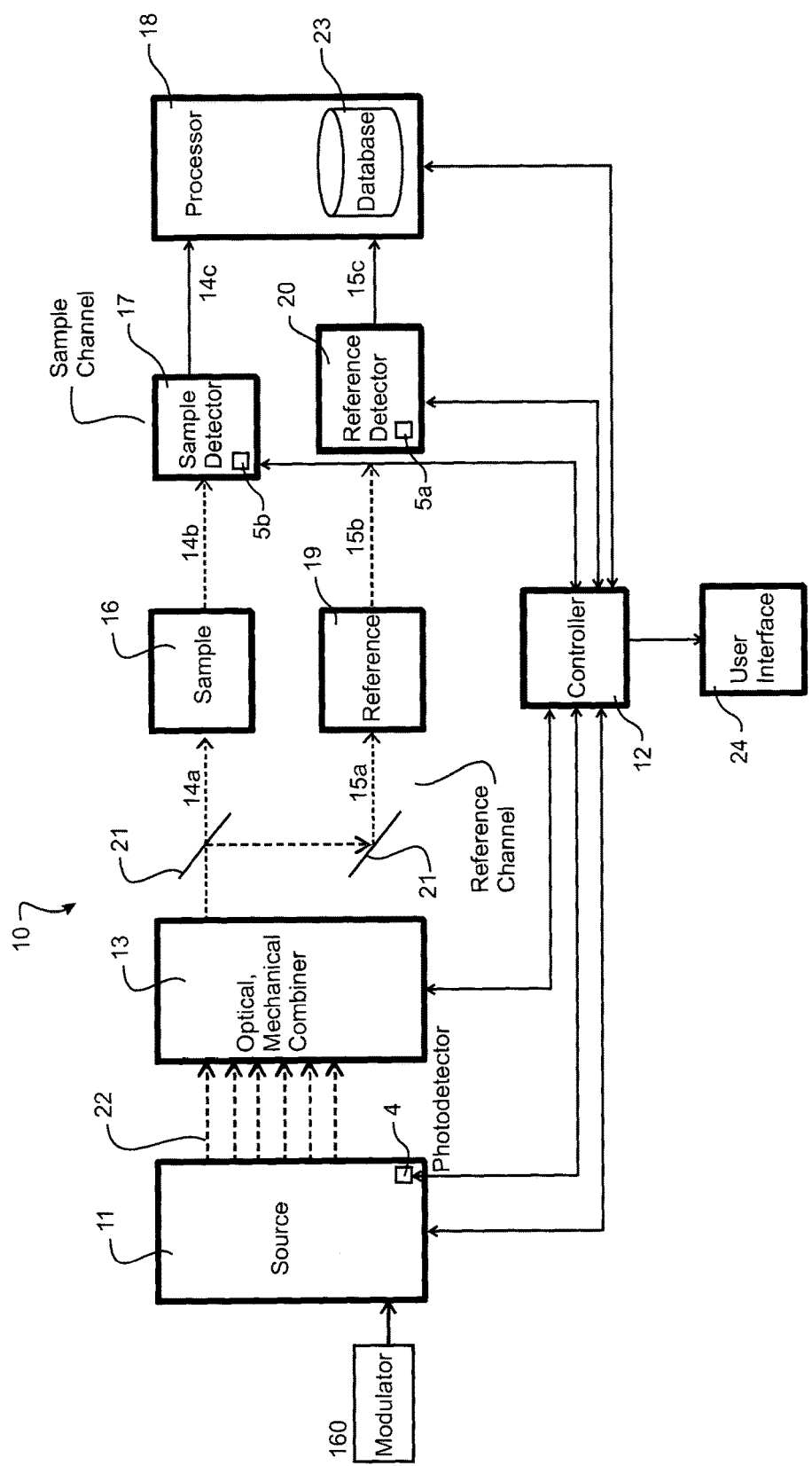
FIG. 18 shows a schematic with a modulator.

In an embodiment described above, a dark current was used to calibrate/normalise the output data from the detectors 17, 20. The dark current is subtracted from the detector reading. In another embodiment, obtaining dark current readings using a chopper wheel (or turning off of the source 11) is not required. Rather, laser driver current modulation is used to eliminate the need for dark current readings. Referring to the simplified schematic of the analyser in FIG. 16, the laser is driven by a driver current/modulator 160. The driver current/modulator may faun part of the source or be separate to it. The source 11 is a laser diode with built-in photodetector 4 (to provide control feedback). A sample cell 16 and photodetector 17 are provided. The laser driver current modulator 160 is also shown in FIG. 18 incorporated into the more detailed block diagram of the overall analyser in FIG. 1.

The sample channel output current is the sum of two components—a dark current term that is present even in the absence of any illumination, and a term proportional to the intensity of light incident on the detector. Therefore, we can write the sample channel output current, $I_S$ as follows:

$$I_S = I_S^{Dark} + S \cdot P \quad (1)$$

where in (1):

$I_S^{Dark}$ is the dark current signal of the sample channel detector

S is a constant representing the attenuation in the optical path including the sample cell.

P is the incident power illuminating the sample cell.

A similar expression can be written for the reference channel output current, $I_R$, generated from the built-in photo-detector of the laser diode source, namely:

$$I_R = I_R^{Dark} + R \cdot P \tag{2}$$

where in (2):

$I_R^{Dark}$ is the dark current signal of the reference photo-detector in the laser diode package.

R is a constant representing the fraction of incident power delivered to the reference.

Figure 17:
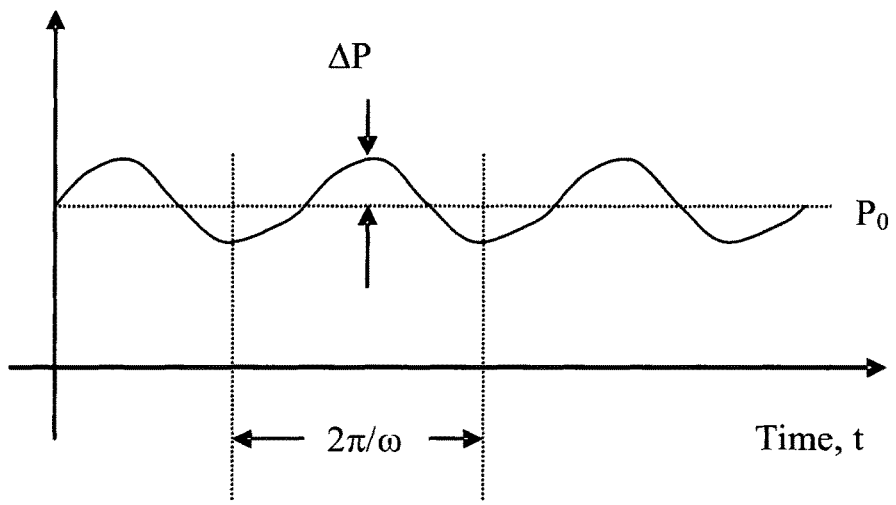
FIG. 17 shows laser output power where the source is modulated.

We now excite the laser source by modulating the driver current with a known waveform. Typically, a sinusoidal modulation with angular frequency ω is used to vary the current about a mean value. This has the effect of modulating the output power of the laser diode source in a similar sinusoidal manner illustrated in FIG. 17.

Mathematically, the time-dependent laser output power, P(t), can be written as follows:

$$P(t) = P_0 + \Delta P \cdot \sin(\omega t + \phi) \tag{3}$$

where in (3):

$P_0$ is the mean output power from the laser $\Delta P$ is the modulation amplitude in the output power waveform (depth of modulation)

$\phi$ is the phase of the modulation waveform at tine, t=0.

If we now substitute for the incident power in equations (1) and (2) using (3), we obtain the following expressions for the output currents from sample and reference channels:

$$I_S = I_S^{Dark} + S \cdot P_0 + S \cdot \Delta P \cdot \sin(\omega t + \phi)$$

$$I_R = I_R^{Dark} + R \cdot P_0 + R \cdot \Delta P \cdot \sin(\omega t + \phi)$$

The parameters of interest with respect to characterising the sample under test are the constants S and R. The ratio of these two constants represents a normalised coefficient characteristic of the liquid in the sample cell.

Expanding the sinusoidal term in the above equations, gives:

$$\sin(\omega t + \phi) = \sin(\omega t)\cos\phi + \cos(\omega t)\sin\phi$$

which gives the following:

$$I_S = I_S^{Dark} + S \cdot P_0 + S \cdot \Delta P \cdot \sin(\omega t)\cos\phi + S \cdot \Delta P \cdot \cos(\omega t)\sin\phi \tag{4}$$

$$\equiv A_{0S} + A_{1S}\cos(\omega t) + B_{1S}\sin(\omega t)$$

$$I_R = I_R^{Dark} + R \cdot P_0 + R \cdot \Delta P \cdot \sin(\omega t)\cos\phi + R \cdot \Delta P \cdot \cos(\omega t)\sin\phi \tag{5}$$

$$\equiv A_{0R} + A_{1R}\cos(\omega t) + B_{1R}\sin(\omega t)$$

So that:

$A_{0S} = I_S^{Dark} + S \cdot P_0$ $A_{0R} = I_R^{Dark} + R \cdot P_0$ $A_{1S} = S \cdot \Delta P \cdot \sin\phi$ $B_{1S} = S \cdot \Delta P \cdot \cos\phi$ $A_{1R} = R \cdot \Delta P \cdot \sin\phi$ $B_{1R} = R \cdot \Delta P \cdot \cos\phi$ Inspection of equations (4) and (5) shows the output currents have the form of a simple Fourier series consisting of constant DC terms, $A_{0S}$ and $A_{0R}$, plus sine and cosine terms that oscillate with the modulation frequency, ω, with amplitudes $A_{1S}$, $A_{1R}$, $B_{1S}$ and $B_{1R}$.

The dark current terms contribute only to the DC term of the Fourier series in (4) and (5). The dark current terms are contained within the DC components of equations (4) and (5). Therefore, a simple Fourier analysis of the modulated output waveform gives the Fourier coefficients of the sin(ωt) and cos(ωt) terms—which are independent of the dark current.

By measuring the sinusoidally varying component of each output current, the constants, S and R, can be determined without the need to measure the dark current of each detector diode. These latter terms can be eliminated from the measurement by DC blocking components or by performing a Fourier analysis of the output currents and discarding all but the sinusoidal terms.

In conventional spectrometer systems, the dark current would be measured by blocking off the illumination to the detector diode using a rotating mechanical chopper that periodically blocks then re-instates the optical illumination. Using the laser-current modulation described above eliminates the need for mechanical components such as rotating choppers which simplifies the spectrometer design, reduces cost and improves reliability by not using any moving parts. Electrical interference from the electric motors used to drive mechanical choppers is also eliminated.

Figure 19:
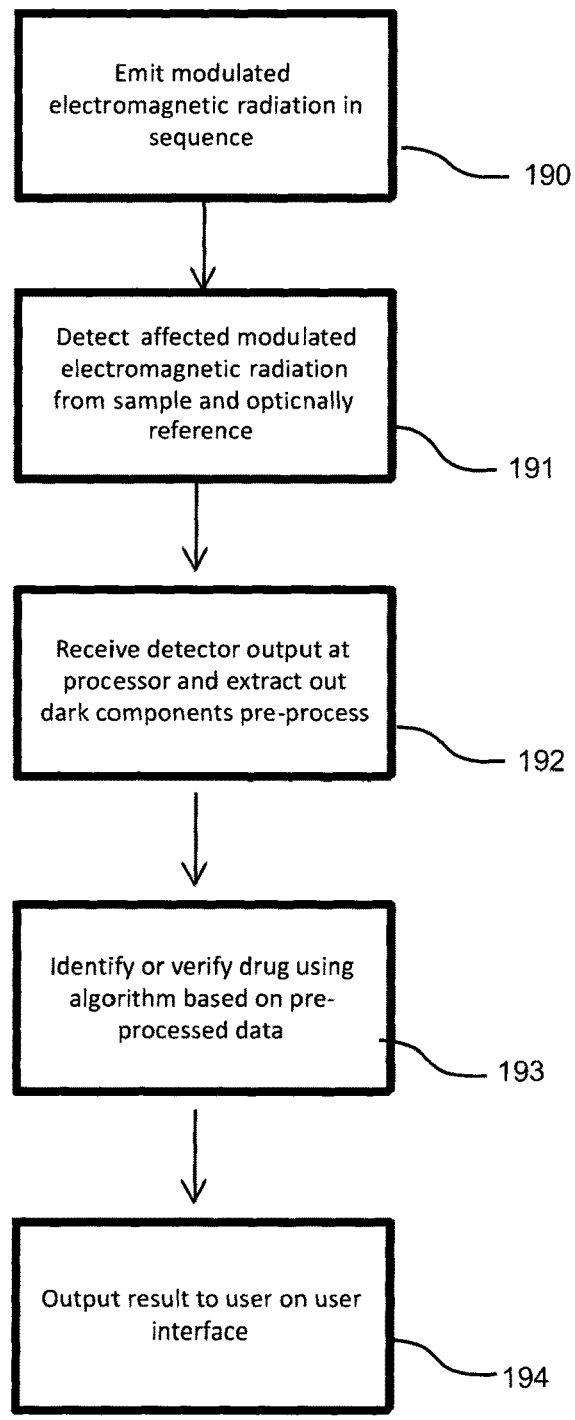
FIG. 19 shows a flow diagram for extracting dark current

The method would work as follows with reference to FIG. 19 which is the same as the method shown in FIG. 4 with the additional dark current method added. The output source electromagnetic radiation would be modulated using the apparatus in FIG. 16/18 and emitted towards the sample step 190. The affected detected radiation would be received by the sample and reference detectors 17 and 20 (where used), step 191 and passed to the processor 18, step 192 for processing. The received output can be processed by the processor step 192 to remove the dark current (DC) component $A_{0S}$ and $A_{0R}$ of the received output (as per equations (4), (5) above) and any other unwanted components. The desired components sin(ωt) and cos(ωt) are obtained and represent the intensity measurement without dark current. This processing can be done using any suitable signal processing know to those in the art. The remaining steps 193 and 194 are as previously described.

For example, in one possibility for extracting dark currently step 192, Fourier analysis of the output currents could be performed by multiplying the outputs by sin(ωt) and cos(ωt) respectively, and integrating over a period of the oscillation. This can be used where the modulation is a single frequency, e.g. sine wave modulation at a single frequency. This procedure provides a form of averaging which is beneficial in reducing measurement noise.

Alternatively, a Fast Fourier Transform (FFT) algorithm can be applied to a digitised output waveform and the relevant Fourier components extracted. From the Fourier coefficients we therefore obtain:

$S \cdot \Delta P = \sqrt{A_{1S}^2 + B_{1S}^2}$ for the sample channel and $R \cdot \Delta P = \sqrt{A_{1R}^2 + B_{1R}^2}$ for the reference channel.

Taking the ratio of these Fourier amplitudes eliminates the dependence on the modulation depth $\Delta P$ to give a normalised output, N, given by:

$$N = \frac{S}{R} \tag{6}$$

Values of N are determined at each wavelength of interest and form the output data set for the liquid under test.

Other methods for extracting the information could be known and used by the skilled in the art.

In an alternative analysis process, a reference channel is not used. Rather, the detector output 14c from affected electromagnetic radiation (from the sample) acquired at an anchor wavelength is used, rather than the detector output 15c from affected electromagnetic radiation from the reference in the reference channel. All other detector output 14c from affected electromagnetic radiation received relating to other wavelengths is normalised/corrected using the detector output of affected electromagnetic radiation at the anchor wavelength. The anchor wavelength can be one of the wavelengths already selected, although preferably will be selected to be in the vicinity or within a region spanning a suitable spectral feature/point in the base liquid spectrum. For example, the anchor wavelength could be in the vicinity of or fall within a region spanning a stable region of the base liquid spectrum. Elimination of the reference channel/detector output removes variation between the sample and reference channels that can mask sample differences, thus removal creates a more sensitive and stable apparatus. The output at the anchor wavelength can be used to normalise, calibrate or otherwise adjust the output for the other wavelengths. The output from the anchor wavelength could be processed in the same manner as the output from the reference channel as describe previously in order to verify/analyse the sample. That is, the anchor output can become the reference information.

In one possibility, where water is the base liquid, 1450 nanometres is chosen as the anchor point as there is particular stability in the spectrum of water around this wavelength. This wavelength corresponds to the maximum optical absorption aqueous solutions due to the presence of OH bonds. It is a common transmission medium for sample drugs tested. Data acquired at this wavelength shows minimum thermal sensitivity and is therefore provides a highly stable and predictable reference. This is just one example for water based drug, and is indicative only and should not be considered limiting as to the wavelengths and anchor points that might be chosen based on other considerations.

Each of the previous embodiments describe the optional use of a reference channel to obtain reference measurements for use in processing data. In an alternative, the reference channel is not used. Rather, a photodiode 4 (see FIG. 20) in the laser diode 11 (which is used for power monitoring and control of the laser diode) can be utilised to obtain reference information. Laser diodes are often fitted with built-in photo-detector diodes 4 that are used to monitor the output power of the laser. This is done to stabilise the laser by allowing the laser driver current to be controlled via a feedback circuit incorporating the integrated photo-diode signal.

This alternative for obtaining reference information can be substituted in place of the reference channel for any of the embodiments described. The reference measurements obtained using the alternative can be utilised in the same manner as described any previous embodiment.

The output of the laser diode photodetector 4 which detects the output power of the source electromagnetic radiation is passed to the processor 18 and used instead of reference readings obtained by the reference detector 20 to normalise and/or correct the output from the detector 17 in the sample channel. This output signal from the photodetector 4 performs the same function as a reference channel that would otherwise have been produced more conventionally by using a beam splitter arrangement involving two separate measurement channels. Using the photo-diode output from the laser as a reference signal thereby eliminates the need for beam-splitting optics and an additional reference sample and detector.

In an alternative embodiment, the electromagnetic source 11 is a broadband source with multiple filters 13 at different wavelengths that can be arranged in between the broadband source and the sample. The output from each filter provides an electromagnetic beam 22 with one of the selected wavelengths. The broadband source could be, for example, a broadband filament blackbody source and filters. The source 11 could alternatively take the form of one or more LEDs with or without filters. Any of the alternative sources could be mounted on a carousel 50 and operated as described for the first embodiment, or operated in conjunction with an optical device such as described in embodiments two to four.

Any of the sources could be temperature stabilised with a feedback system, for example by using thermistors and peltier cooling devices as previously described.

The detectors could be in the form of one or more InGaAs photodiodes or other light sensors.

A separate photodiode or similar or other detector could be used for each of the reference and sample channels. Alternatively, a single photodiode or similar or other detector could be used for both the sample and reference channels, utilising optical devices to merge the affected radiation beams of both channels, or otherwise direct them to the detector.

Random errors in measurements can be reduced by averaging detector readings over many measurements (e.g. 500). Dark measurements (source off) can be used to correct measured data.

For dark current readings, a chopper wheel can optionally be used that blacks out/blocks the electromagnetic radiation 22 incident on the sample 16 and the reference 20. The chopper could form part of the optical device 13. For each electromagnetic reading, the detector 17/20 also takes a "dark" reading when the chopper blocks the electromagnetic radiation 22. Having a chopper wheel and dark reading is not essential for the invention and is described here as one possible option.

Over the band 1300 nm to 2000 nm, it is also possible to use a single type of photo-diode detector based on indium gallium arsenide (InGaAs) technology which further simplifies the detector system.

The present invention preferably uses wavelengths in the analysis region of 1300 nm to 2000 nm or variations thereof. This region has previously been ignored for drug analysis due to the perceived disadvantage of broad spectral peaks and troughs that appear in the absorbance spectrum. Infrared (IR) spectroscopy previously has exploited the numerous narrow-band spectral absorption characteristics that exist for wavelengths longer than 2000 nm. This so-called 'fingerprint' region exhibits spectral lines that are characteristic of certain chemical bonds present in the material under test and offers a highly sensitive technique to identifying the material. The present inventors have determined that the 1300 nm-2000 nm analysis range (or portions thereof) provides an advantage for drug verification or identification or other analysis. Further, the inventors have established that the spectral location of salient spectral features in this analysis region is less affected by temperature variations. The numerous narrow spectral bands that appear in the region above 2000 nm exhibit large temperature sensitivity. If this region above 2000 nm is used for verification or identification, the analysis apparatus requires very precise wavelength resolution. This resolution can only be achieved using high-cost sophisticated spectrometers More particularly, this type of IR spectroscopic measurement (above 2000 nm) requires very fine wavelength resolution (typically a few nanometres) maintained over a wide spectral band in order to resolve the numerous individual spectral features. The fine wavelength resolution is especially required to account for any shift in the narrow spectral lines with respect to temperature variations.

The measurement of such highly resolved spectral lines requires the use of a spectrometer fitted with a sophisticated monochromator based either on a mechanically rotated diffraction grating and single detector, or a fixed grating with a linear array of detector elements. Both options are found in existing spectrometers and both are expensive to implement.

As a cost-effective alternative, aimed for example at water-based intravenous drug verification/identification or other analysis, it has been determined by the present inventors that it is advantageous to make measurements within the shorter wavelength region between 1300 nm and 2000 nm. Whilst the spectral characteristics/features in this wavelength region are much fewer in number and much broader spectrally (differing little from those of water), the inventors have found that there remain sufficient spectral differences between drugs (or other liquid based samples) to facilitate verification/identification. The have also found, that, in the 1300 nm to 2000 nm region, the wavelengths at which the peaks and troughs (and other spectral characteristics) of each drug's IR transmission spectrum occur remain highly stable with respect to temperature for all water-based drugs (or other samples).

Importantly, due to the absence of temperature-sensitive narrow spectral absorption features, they have established there is no requirement for highly resolved spectral lines to be measured thereby eliminating the need for an expensive monochromator. A small number of measurements (5 or 6 typically) made at discrete wavelengths over the range 1300 nm to 2000 nm is sufficient to characterise each drug (or other sample). Typically, each measurement is made over a bandwidth of 12 nm (as determined by a band-pass filter, illuminated by a broad-band source, for example) or over a few nanometres for laser-based illumination.

What is claimed is:

1. An analyser for identifying or verifying a liquid drug for delivery to a patient to reduce risk of adverse drug events, the liquid drug comprising a drug in a base liquid, the liquid drug having a liquid drug spectrum and the base liquid having a base liquid spectrum comprising at least one spectral characteristic feature between substantially 1300 nm and 2000 nm, the analyser comprising:
   an electromagnetic radiation source for emitting electromagnetic radiation at the liquid drug, the electromagnetic radiation comprising a plurality of different wavelengths between substantially 1300 nm and 2000 nm, wherein at least one of the wavelengths is at or in the vicinity of or within a region spanning a wavelength of a spectral characteristic feature of the base liquid spectrum,
   a liquid drug detector that detects affected electromagnetic radiation resulting from the emitted electromagnetic radiation affected by the liquid drug and that provides output representing spectral information of the liquid drug spectrum at the wavelengths, and
   a processor configured to identify or verify the liquid drug from the detector output by:
      querying a database of reference liquid drugs and corresponding spectral information of the reference liquid drugs at the wavelengths, each reference liquid drug comprising a reference drug in a base liquid, each reference liquid drug having a reference liquid drug spectrum and the base liquid having a base liquid spectrum comprising the at least one spectral characteristic feature between substantially 1300 nm and 2000 nm, there being sufficient spectral differences between the reference liquid drug spectrums at the least one spectral characteristic feature of the base liquid spectrum to provide discrimination between reference drugs, and
      identifying or verifying the liquid drug using: a) the detector output representing the spectral information of the liquid drug, and b) the spectral information of the reference liquid drugs, wherein the discrimination between the reference drugs assists with the identifying or verifying the liquid drug.

2. An analyser according to claim 1 wherein the electromagnetic radiation comprises a plurality of electromagnetic radiation beams, each beam having a different wavelength.

3. An analyser according to claim 1 wherein the wavelengths span or capture a plurality of at least some of the spectral characteristic features in the liquid spectrum between 1300 nm and 2000 nm.

4. An analyser according to claim 1 wherein the liquid spectrum comprises two or more spectral characteristic features, and wherein:
   each spectral characteristic feature falls in or spans a region of the liquid spectrum, and
   each wavelength falls within one of the regions.

5. An analyser according to claim 1 wherein the spectral characteristic features comprise peaks, troughs, inflections, stable points or regions, plateaus, knees and/or slopes of the liquid spectrum.

6. An analyser according to claim 1 wherein the source is a plurality of lasers in a single package, each laser configured to emit an electromagnetic radiation beam at a fixed or tuneable wavelength.

7. An analyser according to claim 1 wherein the detector and/or source are temperature compensated to provide temperature stability, using thermistors and peltier devices in a closed loop system.

8. An analyser according to claim 1 wherein the processor, as part of identifying or verifying the liquid drug from the output from the detector:
   turns off the source and measures the output of the detector, resulting in a dark current component, and
   removes the dark current component from the output representing the detected affected electromagnetic radiation.

9. An analyser according to claim 1 wherein the source is further operated to emit electromagnetic radiation at the detector unaffected by the liquid drug, and the processor, as part of identifying or verifying the liquid drug from the output from the detector, measures output of the detector resulting from the emitted electromagnetic radiation unaffected by the liquid drug.

10. A method for identifying or verifying a liquid drug for delivery to a patient to reduce risk of adverse drug events, the liquid drug comprising a drug in a base liquid, the liquid drug having a liquid drug spectrum and the base liquid having a base liquid spectrum comprising at least one spectral characteristic feature between substantially 1300 nm and 2000 nm, the method comprising:
   emitting electromagnetic radiation at the liquid drug, the electromagnetic radiation comprising a plurality of different wavelengths between substantially 1300 nm and 2000 nm, wherein at least one of the wavelengths is at or in the vicinity of or within a region spanning a wavelength of a spectral characteristic feature of the base liquid spectrum, detecting affected electromagnetic radiation resulting from the emitted electromagnetic radiation affected by the liquid drug and providing output representing spectral information of the liquid drug spectrum at the wavelengths, querying a database of reference liquid drugs and corresponding spectral information of the reference liquid drugs at the wavelengths, each reference liquid drug comprising a reference drug in a base liquid, each reference liquid drug having a reference liquid drug spectrum and the base liquid having a base liquid spectrum comprising the at least one spectral characteristic feature between substantially 1300nm and 2000nm, there being sufficient spectral differences between the reference liquid drug spectrums at the least one spectral characteristic feature of the base liquid spectrum to provide discrimination between reference drugs, and identifying or verifying the liquid drug using: a) the output representing the spectral information of the liquid drug, and b) the spectral information of the reference liquid drugs, wherein the discrimination between the reference drugs assists with the identifying or verifying the liquid drug.

11. A method according to claim 10 wherein the electromagnetic radiation comprises a plurality of electromagnetic radiation beams, each beam having a different wavelength.

12. A method according to claim 10 wherein the wavelengths span or capture a plurality of at least some of the spectral characteristic features in the liquid spectrum between 1300 nm and 2000 nm.

13. A method according to claim 10 wherein the liquid spectrum comprises two or more spectral characteristic features, and wherein:
each spectral characteristic feature falls in or spans a region of the liquid spectrum, and
each wavelength falls within one of the regions.

14. A method according to claim 10 wherein the spectral characteristic features comprise peaks, troughs, inflections, stable points or regions, plateaus, knees and/or slopes of the liquid spectrum.

15. A method according to claim 10 wherein the electromagnetic radiation is generated using a source comprising a plurality of lasers, each laser configured to emit an electromagnetic radiation beam at a fixed or tuneable wavelength.

16. A method according to claim 10 wherein the detector and/or source are temperature compensated to provide temperature stability, using thermistors and peltier devices in a closed loop system.

17. A method according to claim 10 further comprising:
turning off the source and measuring the output, resulting in a dark current component, and
removing the dark current component from the output representing the detected affected modulated electromagnetic radiation.

18. A method according to claim 10, wherein the output is provided by a detector, the method further comprising emitting electromagnetic radiation at the detector so it is unaffected by the liquid drug, and measuring the output of the detector resulting from the emitted electromagnetic radiation unaffected by the liquid drug.

* * * * *